(12) United States Patent
Woo et al.

(10) Patent No.: US 6,680,289 B1
(45) Date of Patent: Jan. 20, 2004

(54) METHODS, COMPOSITIONS, AND ARTICLES FOR ODOR CONTROL

(75) Inventors: Ricky Ah-Man Woo, Hamilton, OH (US); Dean Larry DuVal, Lebanon, OH (US); Daniel Scott Cobb, Loveland, OH (US); Robert William Kiblinger, Beckley, WV (US); Hirotaka Uchiyama, Loveland, OH (US); Toan Trinh, Maineville, OH (US)

(73) Assignee: The Proctor & Gamble Company, Cincinnati, OH (US)

( * ) Notice: Subject to any disclaimer, the term of this patent is extended or adjusted under 35 U.S.C. 154(b) by 0 days.

(21) Appl. No.: 09/571,131

(22) Filed: May 15, 2000

Related U.S. Application Data

(60) Provisional application No. 60/152,070, filed on Sep. 2, 1999.

(51) Int. Cl.[7] .................................................. C11D 3/22
(52) U.S. Cl. ....................................... 510/470; 510/101
(58) Field of Search .............................. 510/101, 463, 510/476, 505, 470

(56) References Cited

U.S. PATENT DOCUMENTS

| | | | |
|---|---|---|---|
| 5,441,727 A | 8/1995 | Chatterjee et al. | |
| 5,578,563 A | * 11/1996 | Trinh et al. | 510/513 |
| 5,593,670 A | * 1/1997 | Trinh et al. | 424/76.1 |

FOREIGN PATENT DOCUMENTS

| | | | |
|---|---|---|---|
| JP | 10 053791 | | 2/1998 |
| WO | WO 94/22999 | * | 10/1994 |
| WO | WO 98/07455 | * | 2/1998 |
| WO | WO 98/56890 | | 12/1998 |

* cited by examiner

*Primary Examiner*—John Hardee
(74) *Attorney, Agent, or Firm*—Mark A. Charles; Jeffrey V. Bamber; Jason J. Camp

(57) ABSTRACT

The present invention relates to a method of removing malodor from fabrics; stable, aqueous odor-counteractant composition, preferably for use in the laundry; and articles comprising said composition and instructions for the method and/or benefits to be derived. The composition comprises malodor counteractants such as cyclodextrin, said cyclodextrin being protected from interaction with any other materials that might be present in said composition so as to maintain the cyclodextrin in uncomplexed form and/or, optionally, zeolites, clay, odor blockers, odor reactant such as class I and/or class II aldehydes, essential oil comprising flavanoid, metallic salt, water soluble anionic polymer, etc. to help control odor. Optionally, the composition can also contain low molecular weight polyols, chelating agents, etc. The composition is preferably essentially free of any material that would soil or stain fabric.

25 Claims, No Drawings

METHODS, COMPOSITIONS, AND ARTICLES FOR ODOR CONTROL

CROSS REFERENCE TO RELATED APPLICATION

This application claims the benefit of U.S. Provisional Application Serial No. 60/152,070 filed Sep. 2, 1999 by Woo et al., which is incorporated by reference herein.

TECHNICAL FIELD

The present invention relates to improvements in the laundry process, including the provision of methods to improve the odor of fabrics that retain a malodor after the laundry step. The invention also includes odor-absorbing compositions for use in the laundry, especially concentrated additive compositions that can be used selectively on such fabrics and articles comprising said compositions in association with instructions for practicing the method and/or obtaining the benefits that can be derived from the method. Preferably the compositions restore and/or maintain freshness by reducing malodor.

BACKGROUND OF THE INVENTION

Typical laundry processes remove odors from normal fabrics containing relatively low levels of malodors. However, as the temperature for washing has gotten lower, or when the load has fabrics with high levels of odorants, or when there is some other factor like overloading involved, there is sometimes a lingering malodor. This lingering malodor is different from malodor that is present in some detergent compositions, or is generated after the wash, e.g., by antimicrobial action, or which thereafter becomes attached to the fabrics and is sometimes accompanied by the presence of large amounts of hydrophobic soils. This problem has not been generally recognized, since the general expectation is that the wash cycle removes all odors. However, some consumers have noticed the problem and have taken extreme measures such as doing such fabrics only in separate loads. In general, consumers do not take steps to remove, or counteract the odor, such as, e.g., washing the article again, since the additional measures are not successful. Also, such a second washing is wasteful of time, water, and detergent, and causes increased wear on clothing. Using more detergent is usually undesirable, since that may cause the article to have detergent remaining after the rinse step.

Cyclodextrin has been used to control odors from detergent compositions, to protect perfumes in detergent compositions, improve the solubility of compounds like nonionic surfactants to improve their removal, and like dyes to prevent their transfer to other fabrics by keeping them suspended.

The present invention relates to solving problems associated with having a malodor remaining after the wash process is completed, preferably by the addition of cyclodextrin to help remove/control the malodor, or, less optimally, provide malodor counteractants, like odor blockers or materials that react with the malodors or mask the malodors. The preferred approach uses those materials that result in the removal, or tying up of the malodor. The preferred methods and compositions are used as additives, since the majority of fabric laundry loads do not have the problem and since many of the materials that can neutralize the malodor have their own problems. Cyclodextrin tends to react with perfumes, and surfactants when incorporated in detergent compositions and the level required for malodor control is very high. Odor blockers, when used at the high levels needed for malodor control, block the desirable odors of perfumes as well as the malodors. Similarly, the masking compounds block other desirable odors and reactants can destroy desirable odors.

There is anecdotal information that indicates some consumers may have noticed the problem and have found some ways of solving the problem using materials that are part of the invention herein. However, to avoid causing problems, it is important to provide the general consumer with the identity of the laundry processes, soils, loads, conditions, etc. that typically provide insufficient removal of malodors and the level of ingredients needed to see the benefit. This allows the use of the additive when it is needed. Prior to this invention, the efforts to counteract malodor were based on insufficient information to ensure good results without wasteful use of excess material.

As stated before, in general, provision of such counteractants in the detergent, or fabric softener, is not efficient, since for some loads the benefit is not needed. Also, the level of many ingredients needed to provide good malodor removal/elimination is usually quite high, even for those counteractants that are really effective. Selection of the best counteractant can provide superior results. It is important to avoid the inclusion in the additive compositions of high levels of materials that interfere with the portion of the laundry process where the additive is used. For example, large amounts of acid materials usually hurts detergency by lowering the pH of the wash liquor; anionic materials are usually not compatible with cationic fabric softeners; etc.

SUMMARY OF THE INVENTION

The present invention relates to the method of applying an effective amount of a malodor control agent (counteractant) to at least one step of a laundry process to provide a consumer noticeable improvement in the laundry process by either eliminating malodor, or improving the removal of hydrophobic soils, in an efficient way. Generally, because of the high level of ingredients required for this benefit, it is essential to supply the consumer with the requisite information required to make good decisions, e.g., as to when to use the method by defining the areas of greatest benefit, the amount of malodor counteractant required to provide such a benefit, etc. and providing concentrated compositions and delivery methods that minimize the use of too much or too little counteractant. The compositions are preferably supplied in a package in association with this information. The best counteractants provide some residual malodor prevention effects as well as providing superior end results for the laundry process.

DETAILED DESCRIPTION OF THE INVENTION

I. Method of Use

The compositions described hereinafter can be used by adding an effective amount to fabrics in one, or more of the steps in a typical laundry cycle including a presoak, a wash step, a rinse step, or a water removal step, e.g., wringing or spinning, drying, etc. An effective amount as defined herein means an amount sufficient to absorb or counteract malodor to the point that it is less objectionable, preferably not discernible by the human sense of smell. As discussed herein, for certain odors, the level in the atmosphere around the fabrics, "head space", should be less than the minimum detectable concentration for that odor.

The kinds of soils that are most likely to cause a severe malodor include: soils like those found on mechanics' clothes; food handlers, especially butchers' and kitchen workers' clothes; sewer workers' clothes; bar tenders' clothes; fire fighters' clothes; farm clothes; athletic clothing; factory workers' clothes; heavy machinery operators' clothes; etc. Such soils have an associated malodor that is almost impossible to counteract without the present invention. Such soils also have a relatively high level of hydrophobic soils such as lubricating oil, grease, food oils, body soils, smoke etc. The preferred cyclodextrin malodor counteractant improves the removal of such soils.

For control of malodors, beta cyclodextrin and alpha cyclodextrin are preferred. Gamma cyclodextrin has too large a cavity to control most malodor molecules. Substituted cyclodextrins can be especially valuable where they are more soluble than the corresponding unsubstituted cyclodextrin. The preferred compositions are concentrated and liquid to minimize packaging while maximizing the speed of action. Cyclodextrins can complex with surfactants and perfumes in the wash or rinse waters, thus it is important to disperse the cyclodextrin as soon as possible. It is surprising that the cyclodextrin is not inactivated by, e.g., the surfactant. Using an additive containing cyclodextrin rather than adding cyclodextrin to the detergent or softening composition minimizes the interaction of the cyclodextrin with the ingredients of the detergent and/or softening compositions.

The level of cyclodextrin required for odor removal is high, but it is much less than that required for solubilizing surfactant. Furthermore, it is important that in any detergent composition or softening composition, the cyclodextrin, if present, should be separated (protected) from the actives that could form complexes with the cyclodextrin if one wants to obtain malodor removal from the laundry fabrics. Cyclodextrin that is added to remove odors from the detergent ingredients or to solubilize surfactants is not available for malodor control. Thus the additive compositions used herein to practice the method are preferably substantially free (i.e., there is not enough of the material so that uncomplexed cyclodextrin is still available.) of materials that will complex with the cyclodextrin, such as enzymes, nonionic surfactants that will complex with the cyclodextrin, maltitol hydroxyl aliphatic ether, cationic softener molecules containing straight alkyl chains, fatty acids and their soaps and derivatives thereof, perfumes that complex with the cyclodextrin, etc.

The level of uncomplexed cyclodextrin is related to the soil and/or odor level. The minimum levels are in progressively preferred approximate amounts, especially as the level of soil/odor increase, about 20 ppm, 30 ppm, 40 ppm, and 60 ppm respectively and the maximum levels in increasing order of preference are about 500 ppm, 300 ppm, 200 ppm, and 110 ppm respectively.

The following table illustrates typical methods of use of a concentrated product of the current invention, as disclosed hereinafter, during a wash or rinse cycle.

| Treatment Conditions | Use during wash cycle or rinse cycle |
| --- | --- |
| Machine Type | Kenmore 20 gallon washing machine represents a typical type of top loading washer |
| Laundry Load | Normal Load: about 7 lb |
| Temperature setting | Normal, hot, or cold |
| Typical Directions | Use about ⅓ cup for normal uses, or for extra odor removal use about ½ cup. Add directly to the washing machine during wash cycle or final rinse cycle. (In the instructions for normal usage, the level of composition can vary from about 2 oz to about 3 oz and the level for extra odor removal can vary from about 4 oz to about 8 oz. This is based upon cyclodextrin levels of from about 20 ppm to about 200 ppm, and preferably from about 30 ppm to about 110, by weight of the wash or rinse liquor for normal usage and from about 40 ppm to about 500 ppm, preferably from about 60 ppm to about 300 ppm, by weight of the wash or rinse liquor for extra odor removal.) |

The following examples illustrate the surprising added malodor removal benefit of a typical concentrated composition of the current invention to an AATCC (typical generic detergent formula) powder detergent on fabrics during wash or rinse cycle.

| Method of Use | Dry Grease Odor Grades After Treatment Initial = 90–100* | Dry Synthetic Body Odor Grade After treatment Initial = 90–100* |
| --- | --- | --- |
| ½ Cup AATCC detergent only in wash | 45 | 55 |
| ½ cup AATCC detergent and ⅓ cup odor removal concentrate[1] added during wash cycle | 5 | 15 |
| ½ cup AATCC detergent in wash and ⅓ cup of odor removal concentrate added during final rinse cycle | 0 | 15 |

[1]The concentrate contains: 10% hydroxypropyl beta cyclodextrin, 1%, Silwet L-7600 surfactant, 0.1% perfume, and water..
*The dry fabric odor grades are based upon the evaluation by an expert perfume panel, using a grading scale where 0 = no odor and 100 = extremely strong odor. The final grade is a measure of the overall effectiveness on odor removal with the lower number being better. A 15 units difference in final grade normally represents a consumer noticeable difference in product performance. Furthermore, a final odor grade of less than 20 is generally not detectable by consumer.

As a fabric pretreater, the recommendation is to apply product directly to the soiled fabric evenly. For best results, the instructions are to spray the soiled fabric evenly until slightly damp and then add the garment to the wash.

In the preferred composition, the presence of the surfactant promotes spreading of the solution and the antimicrobial active provides improved odor control as well as antimicrobial action, by minimizing the formation of odors. Both the surfactant and the antimicrobial active provide improved performance and the mixture is especially good.

For compositions containing odor blockers, the level of odor blocker is sufficient to reduce the odor, preferably:from about 0.004 ppm to about 10 ppm, and preferably from about 0.007 to about 5 ppm by weight of the treatment solution, either wash water or rinse water, e.g., the wash or rinse solution in a 20 gallon machine, for normal odor levels and from 0.007 ppm to about 30 ppm and preferably from about 0.01 ppm to about 7 ppm, by weight of the treatment solution for higher odor levels. For materials that react with the odor, like aldehydes, sulfites, etc., the level is preferably: from about 0.05 ppm to about 10 ppm, and preferably from about 0.1 ppm to about 7 ppm, by weight of the treatment solution for normal odor levels and from about 0.1 ppm to about 30 ppm, and preferably from about 0.5 ppm to about 15 ppm, by weight of the treatment solution for higher odor levels. For materials like flavanoids that mask the malodor, the level is preferably: from about 0.1 ppm to about 40 ppm, and preferably from about 0.5 ppm to about 10 ppm, by weight of the treatment solution for normal odor levels and from about 0.2 ppm to about 140 ppm, preferably from about 1 ppm to about 20 ppm by weight of the treatment solution for higher odor levels.

The methods herein are suitable for use with detergent compositions that do not have nonionic detergent surfactants present, or where the level is not sufficient to cause rinsing problems.

The important new information discovered by applicants is that there is a relatively wide spread significant problem associated with high soil loads for some soils as discussed hereinbefore. The problem includes inefficient removal and/ or, especially, malodor associated with these soils. Therefore, it is important that any product containing these odor counteractants have sufficient odor counteractant(s) to provide sufficient reduction in soil and/or odor and that the product, preferably in a package, be in association with instructions to use the product at sufficient levels to provide the benefit(s) and that the soils be identified for the consumer.

In addition to the reduction in soil and/or malodor achieved using the present methods that utilize the compositions described herein, the present methods also encompass methods of preventing malodor from developing on fabrics. Malodor prevention is different from malodor reduction or removal, in that malodor prevention is a proactive method to minimize the possibility for malodor to develop on fabrics, especially after being laundered. Malodor typically develops on clothing fabrics either during "in wear" conditions of the clothing fabrics or during storage of clothing fabrics, such as in closets or environments susceptible to mold or mildew. The development of malodor on clothing fabrics during "in wear" conditions can prove quite embarrassing to the individual wearing the clothing fabrics. The present methods can help prevent these malodors from develop on the clothing fabrics, especially during "in wear" conditions.

The present methods of preventing malodor from developing on fabrics comprises the step of adding an effective amount of the compositions described herein to a wash or rinse cycle of a typical laundry process in order to prevent malodor from developing on the fabrics. To obtain malodor prevention, an effective amount of the malodor counteractants described herein needs to be deposited on the fabrics such that a sufficient amount of the malodor counteractant remains on the fabrics after the washing process to prevent malodor from developing on the fabrics.

A preferred malodor counteractant for preventing malodor from developing on fabrics is cyclodextrin. The present methods of preventing malodor from developing on fabrics preferably further comprises depositing an effective amount of cyclodextrin on the fabrics to prevent malodor. Typically, the amount of cyclodextrin to remain on the fabrics to effectively prevent malodor from developing on the fabrics will be at least about 0.001%, preferably at least about 0.01%, and more preferably at least about 0.1%, by weight of the fabric. Furthermore, it is important to provide instructions to a consumer of the compositions of the present invention in order to communicate the malodor prevention benefits of the compositions and instruct the consumer to use the requisite amounts of the compositions to achieve the benefits.

A preferred composition for use in the malodor prevention methods of the present invention comprise cyclodextrin, a cyclodextrin-compatible surfactant, and a cyclodextrin-compatible antimicrobial active. In using this composition, the amount of antimicrobial active remaining on the fabric to provide malodor prevention is typically at least about 0.001%, preferably at least about 0.01%, and more preferably at least about 0.1%, by weight of the fabric.

II. Composition

A typical representative composition that can be used as an additive for use in the laundry process is an odor-absorbing or neutralizing concentrated composition comprising:

(A) optionally, but preferably, an effective amount to absorb malodors, typically from about 0.1% to about 50% by weight of the composition, preferably from about 1% to about 20%, more preferably from about 3% to about 10% by weight of the composition, of solubilized, uncomplexed cyclodextrin;

(B) optionally, an effective amount of odor blocker typically from about 0.0005% to about 1% by weight of the composition, preferably from about 0.001% to about 0.5%, more preferably from about 0.005% to about 0.2% by weight of the composition;

(C) optionally, an effective amount of class I and/or class II aldehydes typically from about 0.01% to about 1% by weight of composition, preferably from about 0.05% to about 0.5%;

(D) optionally, an effective amount of flavanoid, typically from about 0.01% to about 5%, and preferably from about 0.05% to about 1%, by weight of the composition;

(E) optionally, but preferably, an effective amount of water soluble polymer, especially anionic polymer, e.g. polyacrylic acids or their water soluble salts, at a level of from about 0.001% to about 3%, preferably from about 0.005% to about 2%, more preferably from about 0.01% to about 1% by weight of the composition, for improved odor control benefit;

(F) optionally, an effective amount to improve acceptance of the composition, typically from about 0.03% to about 2%, preferably from about 0.1% to about 1%, more preferably from about 0.2% to about 0.5%, by weight of the composition of a solution, emulsion and/or dispersion comprising perfume in addition to said flavanoids and/or odor blocker, preferably containing at least about 50%, more preferably at least about 60%, and even more preferably at least about 70%, and yet still more preferably at least about 80%, by weight of the perfume of perfume ingredients that have a ClogP of greater than about 3, preferably greater than about 3.5 and a molecular weight of greater than 210, preferably greater than about 220, and/or the particle size of said emulsion or dispersion preferably being large enough that it cannot be complexed by said cyclodextrin, when cyclodextrin is present, and where such perfume can, but preferably doesn't, mask malodor, said perfume, when present, being in addition to the ingredients (B) and/or (C);

(G) optionally, but preferably, an effective amount to improve the performance of the composition, preferably from about 0.01% to about 8%, more preferably from about 0.1% to about 4%, and even more preferably from about 0.5% to about 3%, by weight of the usage composition, of cyclodextrin compatible surfactant that preferably provides a surface tension of from about 20 dyne/cm to about 60 dyne/cm, preferably from about 20 dyne/cm to about 45 dyne/cm;

(H) optionally, at least about 0.01%, preferably at least about 0.05%, and to about 10%, preferably to about 5% by weight, of a soil suspending agent such as a water-soluble substituted or unsubstituted, modified or unmodified polyalkyleneimine soil suspending agent, said soil suspending agent comprising a polyamine backbone;

(I) optionally, an effective amount, to kill, or reduce the growth of microbes, of water soluble antimicrobial active, preferably from about 0.003% to about 2%, more preferably from about 0.01% to about 1.2%, more preferably from about 0.1% to about 0.8%, by weight of the concentrated solution of water soluble antimicrobial active, and said antimicrobial active preferably being selected from the group consisting of halogenated compounds, cyclic nitrogen compounds, quaternary compounds, and phenolic compounds;

(J) optionally, but preferably, from about 0.01% to about 5%, more preferably from about 0.05% to about 2%, and even more preferably from about 0.1% to about 1%, by weight of the usage composition of low molecular weight polyol;

(K) optionally, from about 0.001% to about 1%, preferably from about 0.01% to about 0.3%, more preferably from about 0.02% to about 0.1%, by weight of the usage composition of chelating agent, e.g., aminocarboxylate chelator;

(L) optionally, but preferably, an effective amount of metallic salt, preferably from about 0.1% to about 10%, more preferably from about 0.2% to about 8%, even more preferably from about 0.3% to about 5% by weight of the usage composition, especially water soluble copper and/or zinc salts, for improved odor benefit;

(M) optionally, an effective amount of solubilized, water-soluble, antimicrobial preservative, preferably from about 0.0001% to about 0.5%, more preferably from about 0.0002% to about 0.2%, most preferably from about 0.0003% to about 0.1%, by weight of the composition;

(N) optionally, but preferably, aqueous carrier that optionally can contain up to 20% of a lower molecular weight, water soluble alcohol, said composition containing at least enough of ingredient (A), (B), (C), (D), and/or (E) to provide significant reduction in malodor that survives a typical laundry wash, and preferably being essentially free of any material that would soil or stain fabric under usage conditions, and/or preferably having a pH of more than about 3, more preferably more than about 3.5, and preferably less than about 13, more preferably less than about 12, and said composition preferably being packaged in association with instructions to use it to counteract malodors, optionally identified, that remain after a typical laundry process, said composition being suitable for use as an additive in pre-treating, washing, and/or rinsing of fabrics and containing only low levels of acidic materials and preferably being essentially free of detergent enzymes and/or nonionic surfactants that interact with cyclodextrin when it is present.

The present invention relates more specifically to a concentrated, stable, preferably clear, aqueous odor-absorbing composition, for use in a laundry process such as a pre-soak, washing step, rinse, or drying step, comprising:

(A) an effective amount to absorb malodors, typically from about 1% to about 20%, preferably from about 3% to about 10% by weight of the composition, of solubilized, uncomplexed cyclodextrin;

(B) optionally, an effective amount of odor blocker typically from about 0.0005% to about 1% by weight of the composition, preferably from about 0.001% to about 0.5%, more preferably from about 0.005% to about 0.2% by weight of the composition;

(C) optionally, an effective amount of class I, class II aldehydes, and mixture of typically from about 0.01% to about 1% by weight of composition, preferably from about 0.05% to about 0.5%.

(D) Optionally, an effective amount of flavanoid, typically from about 0.01% to about 5%, preferably from about 0.05% to about 1%, by weight of the composition;

(E) optionally, but preferably, an effective amount of water soluble anionic polymer, e.g. polyacrylic acids and their water soluble salts, from about 0.001% to about 3%, preferably from about 0.005% to about 2%, more preferably from about 0.01% to about 1% by weight of the composition, for improved odor control benefit;

(F) an effective amount to improve acceptance of the composition, typically from about 0.03% to about 2%, preferably from about 0.1% to about 1%, more preferably from about 0.2% to about 0.5%, by weight of the usage composition of a solution, emulsion and/or dispersion comprising perfume in addition to any ingredient already specified, preferably containing at least about 50%, more preferably at least about 60%, and even more preferably at least about 70%, and yet still more preferably at least about 80%, by weight of the perfume of perfume ingredients that have a ClogP of greater than about 3.0, preferably greater than about 3.5 and a molecular weight of greater than about 210, preferably greater than about 220, and/or the particle size of said emulsion or dispersion preferably being large enough that it cannot be complexed by said cyclodextrin, when cyclodextrin is present, and where such perfume can, but preferably doesn't, mask malodor, said perfume, when present, being in addition to the ingredients (B) and/or (C);

(G) optionally, an effective amount to improve the performance of the composition, preferably from about 0.01% to about 8%, preferably from about 0.2% to about 4%, more preferably from about 0.3% to about 3%, by weight of the composition, of cyclodextrin compatible surfactant that preferably provides a surface tension of from about 20 dyne/cm to about 60 dyne/cm, preferably from about 20 dyne/cm to about 45 dyne/cm;

(H) optionally, at least about 0.01%, preferably at least about 0.05%, and to about 10%, preferably to about 5% by weight, of a soil suspending agent such as a water-soluble substituted or unsubstituted, modified or unmodified polyalkyleneimine soil suspending agent, said soil suspending agent comprising a polyamine backbone;

(I) optionally, an effective amount, to kill, or reduce the growth of microbes, of water soluble antimicrobial active which is compatible with the other ingredients, preferably from about 0.001% to about 2%, preferably from about 0.01% to about 1.2%, more preferably from about 0.1% to about 0.8%, by weight of the composition, and preferably selected from the group consisting of halogenated compounds, cyclic nitrogen compounds, quaternary compounds, and phenolic compounds;

(J) optionally, but preferably, from about 0.01% to about 6%, more preferably from about 0.05% to about 3%, and even more preferably from about 0.1% to about 2%, by weight of the composition of low molecular weight polyol;

(K) optionally, from about 0.001% to about 1%, preferably from about 0.01% to about 0.5%, more preferably from about 0.02% to about 0.1%, by weight of the usage composition of chelator, e.g., aminocarboxylate chelator;

(L) optionally, but preferably, an effective amount of metallic salt, preferably from about 0.1% to about 10%, more preferably from about 0.2% to about 8%, even more preferably from about 0.3% to about 5% by weight of the composition, especially water soluble copper and/or zinc salts, for improved odor benefit;

(M) optionally, an effective amount of enzyme, from about 0.0001% to about 0.5%, preferably from about 0.001% to about 0.3%, more preferably from about 0.005% to about 0.2% by weight of the composition, for improved odor control benefit;

(N) optionally, an effective amount of solubilized, water-soluble, antimicrobial preservative, preferably from about 0.0001% to about 0.5%, more preferably from about 0.0002% to about 0.2%, most preferably from about 0.0003% to about 0.1%, by weight of the composition;

(O) the balance being aqueous carrier that optionally can contain up to about 20% lower molecular weight water soluble alcohol, said composition containing at least enough of ingredient (A), (B), (C) and/or (D), to provide significant reduction in malodor that survives a typical laundry wash, and said composition preferably being essentially free of any material that would soil or stain fabric under usage conditions, and/or preferably having a pH of more than about 3, more preferably more than about 3.5, and preferably less than about 13, more preferably less than about 12, and said composition preferably being packaged in association with instructions to use it to counteract malodors that remain after a typical laundry process, said composition being suitable for use as an additive in pretreating, washing, and/or rinsing of fabrics, more preferably with specific instructions, as set forth hereinbefore as to levels of use, and types of odors to treat, and containing only low levels of acidic materials and preferably being essentially free of detergent enzymes.

(A) Cyclodextrin

As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in donut-shaped rings. The specific coupling and conformation of the glucose units give the cyclodextrins a rigid, conical molecular structures with hollow interiors of specific volumes. The "lining" of each internal cavity is formed by hydrogen atoms and glycosidic bridging oxygen atoms; therefore, this surface is fairly hydrophobic. The unique shape and physical-chemical properties of the cavity enable the cyclodextrin molecules to absorb (form inclusion complexes with) organic molecules or parts of organic molecules which can fit into the cavity. Many odorous molecules can fit into the cavity including many malodorous molecules and perfume molecules. Therefore, cyclodextrins, and especially mixtures of cyclodextrins with different size cavities, can be used to control odors caused by a broad spectrum of organic odoriferous materials, which may, or may not, contain reactive functional groups. The complexation between cyclodextrin and odorous molecules occurs rapidly in the presence of water. However, the extent of the complex formation also depends on the polarity of the absorbed molecules. In an aqueous solution, strongly hydrophilic molecules (those which are highly water-soluble) are only partially absorbed, if at all. Therefore, cyclodextrin does not complex effectively with some very low molecular weight organic amines and acids when they are present at low levels on wet fabrics. As the water is being removed however, e.g., the fabric is being dried off, some low molecular weight organic amines and acids have more affinity and will complex with the cyclodextrins more readily.

The cavities within the cyclodextrin in the solution of the present invention should remain essentially unfilled (the cyclodextrin remains uncomplexed) while in solution, in order to allow the cyclodextrin to absorb various odor molecules when the solution is applied to a surface. Non-derivatised (normal) beta-cyclodextrin can be present at a level up to its solubility limit of about 1.85% (about 1.85 g in 100 grams of water) under the conditions of use at room temperature.

Preferably, the odor absorbing solution of the present invention is clear. The term "clear" as defined herein means transparent or translucent, preferably transparent, as in "water clear," when observed through a layer having a thickness of less than about 10 cm. However, one can suspend undissolved cyclodextrin such as beta-cyclodextrin, uniformly in a higher viscosity liquid or gel Preferably, the cyclodextrins used in the present invention are highly water-soluble such as, alpha-cyclodextrin and/or derivatives thereof, gamma-cyclodextrin and/or derivatives thereof, derivatised beta-cyclodextrins, and/or mixtures thereof. The derivatives of cyclodextrin consist mainly of molecules wherein some of the OH groups are converted to OR groups. Cyclodextrin derivatives include, e.g., those with short chain alkyl groups such as methylated cyclodextrins, and ethylated cyclodextrins, wherein R is a methyl or an ethyl group; those with hydroxyalkyl substituted groups, such as hydroxypropyl cyclodextrins and/or hydroxyethyl cyclodextrins, wherein R is a $—CH_2—CH(OH)—CH_3$ or a $^-CH_2CH_2—OH$ group; branched cyclodextrins such as maltose-bonded cyclodextrins; cationic cyclodextrins such as those containing 2-hydroxy-3-(dimethylamino)propyl ether, wherein R is $CH_2—CH(OH)—CH_2—N(CH_3)_2$ which is cationic at low pH; quaternary ammonium, e.g., 2-hydroxy-3-(trimethylammonio) propyl ether chloride groups, wherein R is $CH_2—CH(OH)—CH_2—N^+(CH_3)_3Cl^-$; anionic cyclodextrins such as carboxymethyl cyclodextrins, cyclodextrin sulfates, and cyclodextrin succinylates; amphoteric cyclodextrins such as carboxymethyl/quaternary ammonium cyclodextrins; cyclodextrins wherein at least one glucopyranose unit has a 3-6-anhydro-cyclomalto structure, e.g., the mono-3-6-anhydrocyclodextrins, as disclosed in "Optimal Performances with Minimal Chemical Modification of Cyclodextrins", F. Diedaini-Pilard and B. Perly, The 7th International Cyclodextrin Symposium Abstracts, April 1994, p. 49, said references being incorporated herein by reference; and mixtures thereof. Other cyclodextrin derivatives are disclosed in U.S. Pat. No. : 3,426,011, Parmerter et al., issued Feb. 4, 1969; U.S. Pat. Nos. 3,453,257; 3,453, 258; 3,453,259; and 3,453,260, all in the names of Parmerter et al., and all issued Jul. 1, 1969; U.S. Pat. No. 3,459,731, Gramera et al., issued Aug. 5, 1969; U.S. Pat. No. 3,553,191, Parmerter et al., issued Jan. 5, 1971; U.S. Pat. No. 3,565, 887, Parmerter et al., issued Feb. 23, 1971; U.S. Pat. No. 4,535,152, Szejtli et al., issued Aug. 13, 1985; U.S. Pat. No. 4,616,008, Hirai et al., issued Oct. 7, 1986; U.S. Pat. No. 4,678,598, Ogino et al., issued Jul. 7, 1987; U.S. Pat. No. 4,638,058, Brandt et al., issued Jan. 20, 1987; and U.S. Pat. No. 4,746,734, Tsuchiyama et al., issued May 24, 1988; all of said patents being incorporated herein by reference. Further cyclodextrin derivatives suitable herein include those disclosed in V. T. D'Souza and K. B. Lipkowitz, Chemical Reviews: Cyclodextrins, Vol. 98, No. 5 (American Chemical Society, July/August 1998), which is incorporated herein by reference.

Highly water-soluble cyclodextrins are those having water solubility of at least about 10 g in 100 ml of water at room temperature, preferably at least about 20 g in 100 ml of water, more preferably at least about 25 g in 100 ml of water at room temperature. The availability of solubilized, uncomplexed cyclodextrins is essential for effective and efficient odor control performance. Solubilized, water-soluble cyclodextrin can exhibit more efficient odor control performance than non-water-soluble cyclodextrin when deposited onto surfaces, especially fabric.

Examples of preferred water-soluble cyclodextrin derivatives suitable for use herein are hydroxypropyl alpha-cyclodextrin, methylated alpha-cyclodextrin, methylated beta-cyclodextrin, hydroxyethyl beta-cyclodextrin, and hydroxypropyl beta-cyclodextrin. Hydroxyalkyl cyclodextrin derivatives preferably have a degree of substitution of from about 1 to about 14, more preferably from about 1.5 to about 7, wherein the total number of OR groups per cyclodextrin is defined as the degree of substitution. Methylated cyclodextrin derivatives typically have a degree of substitution of from about 1 to about 18, preferably from about 3 to about 16. A known methylated beta-cyclodextrin is heptakis-2,6-di-O-methyl-β-cyclodextrin, commonly known as DIMEB, in which each glucose unit has about 2 methyl groups with a degree of substitution of about 14. A preferred, more commercially available, methylated beta-cyclodextrin is a randomly methylated beta-cyclodextrin, commonly known as RAMEB, having different degrees of substitution, normally of about 12.6. RAMEB is more preferred than DIMEB, since DIMEB affects the surface activity of the preferred surfactants more than RAMEB. The preferred cyclodextrins are available, e.g., from Cerestar USA, Inc. and Wacker Chemicals (USA), Inc.

It is also preferable to use a mixture of cyclodextrins. Such mixtures absorb odors more broadly by complexing with a wider range of odoriferous molecules having a wider range of molecular sizes. Preferably at least a portion of the cyclodextrins is alpha-cyclodextrin and its derivatives thereof, gamma-cyclodextrin and its derivatives thereof, and/or derivatised beta-cyclodextrin, more preferably a mixture of alpha-cyclodextrin, or an alpha-cyclodextrin derivative, and derivatised beta-cyclodextrin, even more preferably a mixture of derivatised alpha-cyclodextrin and derivatised beta-cyclodextrin, most preferably a mixture of hydroxypropyl alpha-cyclodextrin and hydroxypropyl beta-cyclodextrin, and/or a mixture of methylated alpha-cyclodextrin and methylated beta-cyclodextrin.

Uncomplexed cyclodextrin molecules, which are made up of varying numbers of glucose units provide the absorbing advantages of known absorbent deodorizing compositions without harmful effects to fabrics. While cyclodextrin is an effective odor absorbing active, some small molecules are not sufficiently absorbed by the cyclodextrin molecules because the cavity of the cyclodextrin molecule may be too large to adequately hold the smaller organic molecule. If a small sized organic odor molecule is not sufficiently absorbed into the cyclodextrin cavity, a substantial amount of malodor can remain. In order to alleviate this problem, low molecular weight polyols can be added to the composition as discussed hereinafter, to enhance the formation of cyclodextrin inclusion complexes. Furthermore, optional water soluble metal salts can be added as discussed hereinafter, to complex with some nitrogen-containing and sulfur-containing malodor molecules.

Since cyclodextrin is a prime breeding ground for certain microorganisms, especially when in aqueous compositions, it is preferable to include a water-soluble antimicrobial preservative, which is effective for inhibiting and/or regulating microbial growth, to increase storage stability of aqueous odor-absorbing solutions containing water-soluble cyclodextrin, when the composition does not contain an antimicrobial material as described hereinafter.

It is also desirable to provide optional ingredients such as a cyclodextrin compatible antimicrobial active that provides substantial kill of organisms that cause, e.g., odor, infections, etc. It is also desirable that the compositions contain a cyclodextrin compatible surfactant to promote spreading of the odor absorbing composition on hydrophobic surfaces such as polyester, nylon, etc. as well as to penetrate any oily, hydrophobic soil for improved malodor control. Furthermore, it is desirable that the cyclodextrin-compatible surfactant provide in-wear electrostatic control. It is more preferable that the odor absorbing composition of the present invention contain both a cyclodextrin-compatible antibacterial active and a cyclodextrin-compatible surfactant. A cyclodextrin-compatible active is one which does not substantially form a complex with cyclodextrin in the composition, at the usage concentration, so that an effective amount of both the free, uncomplexed active and free, uncomplexed cyclodextrin are available for their intended uses. Furthermore, it is desirable to include a humectant to maintain a desirable moisture level in cotton fabrics while they dry to maximize dewrinkling.

For controlling odor on fabrics, the composition is preferably used as an additive to the washing step of a laundry process to maximize the odor removal and to take advantage of the cleaning benefit that can be achieved by the use of high levels of cyclodextrin. Specifically, soils that contain high levels of hydrophobic, oily soils, can be removed more completely by the addition of cyclodextrin. This more complete removal is partly due to solubilization from the fabric and partly due to the suspension of the soil. Cyclodextrin also provides softening and anti-wrinkling benefits when used at these high levels. Surprisingly, the interaction of the cyclodextrin and surfactants is minimal when the cyclodextrin is added as part of an additive due to the lack of time and/or concentration required to form complexes.

While a more dilute composition can be used, concentrated compositions are preferably used in order to deliver a less expensive and/or less bulky product, i.e., when the level of cyclodextrin used is from about 2% to about 60%, more preferably from about 3% to about 30%, by weight of the concentrated composition.

(B) Odor Blockers

Although not preferred, odor blockers can be used to mitigate the effects of malodors. In order to be effective, the blockers normally have to be present at all times. If the odor blocker evaporates before the source of the odor is gone, it is less likely to control the odor. Also, the odor blockers tend to adversely affect aesthetics by blocking the wanted odors like perfumes.

Suitable odor "blockers" are disclosed in U.S. Pat. Nos. 4,009,253; 4,187,251, 4,719,105; 5,441,727; and 5,861,371, said patents being incorporated herein by reference.

(C) Aldehydes

As an optional ingredient, aldehydes can be used to mitigate the effects of malodors. Suitable aldehydes are class I, class II aldehydes, and mixture of such aldehydes that are disclosed in U.S. Pat. No. 5,676,163, said patent being incorporated herein by reference.

(D) Flavanoids

Flavanoids are ingredients found in typical essential oils. Such oils include essential oil extracted by dry distillation from needle leaf trees and grasses such as cedar, Japanese cypress, eucalyptus, Japanese red pine, dandelion, low striped bamboo and cranesbill and it contains terpenic material such as alpha-pinene, beta-pinene, myrcene, phencone and camphene. The terpene type substance is homogeneously dispersed in the finishing agent by the action of nonionic surfactant and is attached to fibres constituting the cloth. Also included are extracts from tea leaf. Descriptions of such materials can be found in JP6219157, JP 02284997, JP04030855, etc. said references being incorporated herein by reference.

(E) Perfume

The odor absorbing composition of the present invention can also provide a "scent signal" in the form of a pleasant odor which signals the removal of malodor from fabrics. The perfume herein is in addition to perfume ingredients that fulfill the role of odor counteractant, and are designed to provide, at least in part, a lasting perfume scent. Perfume is added at levels of from about 0% to about 1%, preferably from about 0.003% to about 0.3%, more preferably from about 0.005% to about 0.2%, by weight of the usage composition.

Perfume is added to provide a more lasting odor on surfaces. When stronger levels of perfume are preferred, relatively higher levels of perfume can be added. Any type of perfume can be incorporated into the composition of the present invention so long as the preferred hydrophobic perfume that will complex with the cyclodextrin is formed into an emulsion with a droplet size that will not readily interact with the cyclodextrin in the composition. The perfume ingredients can be either hydrophilic or hydrophobic.

If the perfume ingredients are hydrophilic, they should be dissolved in the aqueous phase so they do not complex with the cyclodextrin when it is present. It is important to note that for best product stability and improved cyclodextrin compatibility, a clear premix consisting of hydrophilic perfume ingredients, cyclodextrin compatible surfactant, and solubility aid (for example, ethanol) is firstly made so that all hydrophilic perfume ingredients are pre-dissolved. Cyclodextrin, water hold and optional ingredients are always added during the final mixing stage. In order to reserve an effective amount of cyclodextrin molecules for odor control, hydrophilic perfume ingredients are typically present at a level wherein less than about 90% of the cyclodextrin complexes with the perfume, preferably less than about 50% of the cyclodextrin complexes with the perfume, more preferably, less than about 30% of the cyclodextrin complexes with the perfume, and most preferably, less than about 10% of the cyclodextrin complexes with the perfume. The cyclodextrin to perfume weight ratio should be greater than about 8:1, preferably greater than about 10:1, more preferably greater than about 20:1, even more preferably greater than 40:1 and most preferably greater than about 70:1.

Hydrophilic perfumes are composed predominantly of ingredients having a ClogP of less than about 3.5, more preferably less than about 3 and, preferably, lower molecular weights, e.g., below about 220, preferably below about 210. If longer lasting perfume effects are desired, the hydrophobic perfumes disclosed below are used.

(a) Hydrophobic Perfume Ingredients

In order to provide long lasting effects, the perfume is at least partially hydrophobic and has a relatively high boiling point. I.e., it is composed predominantly of ingredients selected from two groups of ingredients, namely, (a) hydrophilic ingredients having a ClogP of more than about 3, more preferably more than about 3.5, and (b) ingredients having a molecular weight above about 210, preferably above about 220. Typically, at least about 50%, preferably at least about 60%, more preferably at least about 70%, and most preferably at least about 80% by weight of the perfume is composed of perfume ingredients of the above groups (a) and (b). For these preferred perfumes, the cyclodextrin to perfume weight ratio is typically of from about 2:1 to about 200:1; preferably from about 4:1 to about 100:1, more preferably from about 6:1 to about 50:1, and even more preferably from about 8:1 to about 30:1.

Hydrophobic perfume ingredients have a tendency to complex with the cyclodextrins. The degree of hydrophobicity of a perfume ingredient can be correlated with its octanol/water partition coefficient P. The octanol/water partition coefficient of a perfume ingredient is the ratio between its equilibrium concentration in octanol and in water. A perfume ingredient with a greater partition coefficient P is considered to be more hydrophobic. Conversely, a perfume ingredient with a smaller partition coefficient P is considered to be more hydrophilic. Since the partition coefficients of the perfume ingredients normally have high values, they are more conveniently given in the form of their logarithm to the base 10, logP. Thus the preferred perfume hydrophobic perfume ingredients of this invention have a logP of about 3 or higher, preferably of about 3.5 or higher.

The logP of many perfume ingredients have been reported; for example, the Pomona92 database, available from Daylight Chemical Information Systems, Inc. (Daylight CIS), Irvine, Calif., contains many, along with citations to the original literature. However, the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each perfume ingredient, and takes into account the numbers and types of atoms, the atom connectivity, and chemical bonding. The ClogP values, which are the most reliable and widely used estimates for this physicochemical property, are used instead of the experimental logP values in the selection of perfume ingredients which are useful in the present invention.

Non-limiting examples of the more preferred hydrophobic (enduring) perfume ingredients are selected from the group consisting of: diethyl phthalate, methyl dihydro jasmonate, lyral, hexyl salicylate, iso-E super, hexyl cinnamic aldehyde, iso-propyl myristate, galaxolide, phenyl-ethyl-phenyl acetate, cis-jasmone; dimethyl benzyl carbinyl acetate; ethyl vanillin; geranyl acetate; alpha-ionone; beta-ionone; gamma-ionone; lauric aldehyde; methyl dihydrojasmonate; methyl nonyl acetaldehyde; gamma-nonalactone; phenoxy ethyl iso-butyrate; phenyl ethyl dimethyl carbinol; phenyl ethyl dimethyl carbinyl acetate; alpha-methyl-4-(2-methylpropyl)-benzenepropanal (Suzaral T); 6-acetyl-1,1,3,4,4,6-hexamethyl tetrahydronaphthalene (Tonalid); undecylenic aldehyde; vanillin; 2,5,5-trimethyl-2-pentyl-cyclopentanone (veloutone); 2-tert-butylcyclohexanol (verdol); verdox; para-tert-butylcyclohexyl acetate (vertenex); and mixtures thereof. Enduring perfume compositions can be formulated using these enduring perfume ingredients, preferably at a level of at least about 5%, more preferably at least about 10%, and even more preferably at least about 20%, by weight of the enduring perfume composition, the total level of enduring perfume ingredients, as disclosed herein, being at least about 70%, all by weight of said enduring perfume composition.

Other enduring perfume ingredients that can be used with the above named enduring perfume ingredients can be characterized by boiling point (B.P.) and octanol/water partitioning coefficient (P). The octanol/water partitioning coefficient of a perfume ingredient is the ratio between its equilibrium concentrations in octanol and in water. These other enduring perfume ingredients of this invention have a molecular weight of more than about 210, preferably more than about 220; and an octanol/water partitioning coefficient P of about 1,000 or higher. Since the partitioning coefficients of these other enduring perfume ingredients of this invention have high values, they are more conveniently given in the form of their logarithm to the base 10, logP. Thus these other enduring perfume ingredients of this invention have logP of about 3 or higher, preferably more than about 3.1, and even more preferably more than about 3.2.

The following table illustrates the molecular weight property of some of the preferred perfume versus non-preferred perfume components.

| Examples of Perfume Components for CD Interaction | | |
|---|---|---|
| Perfume component | Molecular weight | CD interaction |
| Diethyl Phthalate | 222.0 | weak |
| Methyl Dihydro Jasmonate | 226.3 | weak |
| Lyral | 210.3 | weak |
| Hexyl Salicylate | 222.3 | weak |
| Iso-E Super | 234.0 | weak |
| Hexyl cinnamic Aldehyde | 216.3 | weak |
| Iso-propyl Myristate | 270.0 | weak |
| Galaxolide | 258 | weak |
| Tonalid | 258 | weak |
| Phenyl-Ethyl-Phenyl Acetate | 240 | weak |
| Tetrahydrolinalol | 158.0 | significant |
| Koavone | 182.0 | strong |
| Terpinyl Acetate | 196.0 | significant |
| Vertenex | 198.3 | strong |
| Flor Acetate | 192.0 | strong |
| a-ionone | 192.3 | strong |
| Cymal | 170.0 | strong |
| a-Me Ionone | 206.3 | strong |
| Frutene | 206.0 | strong |
| Lilial | 204.3 | strong |

Nonlimiting examples of other preferred hydrophobic perfume ingredients which can be used in perfume compositions of this invention are:

| Examples of Other Enduring Perfume Ingredients | | |
|---|---|---|
| Perfume Ingredients | Approximate B.P. (° C.) (a) | ClogP |
| Allyl cyclohexane propionate | 267 | 3.935 |
| Ambrettolide | 300 | 6.261 |
| Ambrox DL (Dodecahydro-3a,6,6,9a-tetramethyl-naphtho[2,1-b]furan) | 250 | 5.400 |
| Amyl benzoate | 262 | 3.417 |
| Amyl cinnamate | 310 | 3.771 |
| Amyl cinnamic aldehyde | 285 | 4.324 |
| Amyl cinnamic aldehyde dimethyl acetal | 300 | 4.033 |
| iso-Amyl salicylate | 277 | 4.601 |
| Aurantiol | 450 | 4.216 |
| Benzophenone | 306 | 3.120 |
| Benzyl salicylate | 300 | 4.383 |
| para-tert-Butyl cyclohexyl acetate | +250 | 4.019 |
| iso-Butyl quinoline | 252 | 4.193 |
| beta-Caryophyllene | 256 | 6.333 |
| Cadinene | 275 | 7.346 |
| Cedrol | 291 | 4.530 |
| Cedryl acetate | 303 | 5.436 |
| Cedryl formate | +250 | 5.070 |
| Cinnamyl cinnamate | 370 | 5.480 |
| Cyclohexyl salicylate | 304 | 5.265 |
| Cyclamen aldehyde | 270 | 3.680 |
| Dihydro isojasmonate | +300 | 3.009 |
| Diphenyl methane | 262 | 4.059 |
| Diphenyl oxide | 252 | 4.240 |
| Dodecalactone | 258 | 4.359 |
| iso E super | +250 | 3.455 |
| Ethylene brassylate | 332 | 4.554 |
| Ethyl methyl phenyl glycidate | 260 | 3.165 |
| Ethyl undecylenate | 264 | 4.888 |
| Exaltolide | 280 | 5.346 |
| Galaxolide | +250 | 5.482 |
| Geranyl anthranilate | 312 | 4.216 |
| Geranyl phenyl acetate | +250 | 5.233 |
| Hexadecanolide | 294 | 6.805 |
| Hexenyl salicylate | 271 | 4.716 |
| Hexyl cinnamic aldehyde | 305 | 5.473 |
| Hexyl salicylate | 290 | 5.260 |
| alpha-Irone | 250 | 3.820 |
| Lilial (p-t-bucinal) | 258 | 3.858 |
| Linalyl benzoate | 263 | 5.233 |
| 2-Methoxy naphthalene | 274 | 3.235 |
| gamma-n-Methyl ionone | 252 | 4.309 |
| Musk indanone | +250 | 5.458 |
| Musk ketone | MP = 137° C. | 3.014 |
| Musk tibetine | MP = 136° C. | 3.831 |
| Myristicin | 276 | 3.200 |
| Oxahexadecanolide-10 | +300 | 4.336 |
| Oxahexadecanolide-11 | MP = 35° C. | 4.336 |
| Patchouli alcohol | 285 | 4.530 |
| Phantolide | 288 | 5.977 |
| Phenyl ethyl benzoate | 300 | 4.058 |
| Phenyl ethyl phenyl acetate | 325 | 3.767 |
| Phenyl heptanol | 261 | 3.478 |
| Phenyl hexanol | 258 | 3.299 |
| alpha-Santalol | 301 | 3.800 |
| Thibetolide | 280 | 6.246 |
| delta-Undecalactone | 290 | 3.830 |
| gamma-Undecalactone | 297 | 4.140 |
| Undecavertol (4-methyl-3-decen-5-ol) | 250 | 3.690 |
| Vetiveryl acetate | 285 | 4.882 |
| Yara-yara | 274 | 3.235 |
| Ylangene | 250 | 6.268 |

BP ≧ 250° C. and ClogP ≧ 3.0
(a) M.P. is melting point; these ingredients have a B.P. (boiling point) higher than about 250° C.

The preferred perfume compositions used in the present invention contain at least 4 different hydrophobic perfume ingredients, preferably at least 5 different hydrophobic perfume ingredients, more preferably at least 6 different hydrophobic perfume ingredients, and even more preferably at least 7 different hydrophobic perfume ingredients. Most common perfume ingredients which are derived from natural sources are composed of a multitude of components. When each such material is used in the formulation of the preferred perfume compositions of the present invention, it is counted as one single ingredient, for the purpose of defining the invention.

Low Odor Detection Threshold Perfume Ingredient

The composition can also contain low to moderate levels of low odor detection threshold materials, either dissolved in the aqueous phase to the extent of their water solubility or incorporated into the emulsion or dispersion with the other hydrophobic perfume ingredients. The odor detection threshold is the lowest vapor concentration of that material which can be olfactorily detected. The odor detection threshold and some odor detection threshold values are discussed in, e.g., "Standardized Human Olfactory Thresholds", M. Devos et al, IRL Press at Oxford University Press, 1990, and "Compilation of Odor and Taste Threshold Values Data", F. A. Fazzalari, editor, ASTM Data Series DS 48A, American Society for Testing and Materials, 1978, both of said publications being incorporated by reference. The use of small amounts of perfume ingredients that have low odor detection threshold values can improve perfume odor character. Perfume ingredients that have a significantly low detection threshold, useful in the composition of the present invention, are selected from the group consisting of ambrox, bacdanol, benzyl salicylate, butyl anthranilate, cetalox, damascenone, alpha-damascone, gamma-dodecalactone, ebanol, herbavert, cis-3-hexenyl salicylate, alpha-ionone, beta-ionone, alpha-isomethylionone, lilial, methyl nonyl ketone, gamma-undecalactone, undecylenic aldehyde, and mixtures thereof. These materials are preferably present at low levels, typically less than about 30%, preferably less than about 20%, more preferably less than about 15%, by weight of the total perfume compositions of the present invention. However, only low levels are required to provide an effect.

There are also hydrophilic ingredients that have a significantly low detection threshold, and are especially useful in the composition of the present invention. Examples of these ingredients are allyl amyl glycolate, anethole, benzyl acetone, calone, cinnamic alcohol, coumarin, cyclogalbanate, Cyclal C, cymal, 4-decenal, dihydro isojasmonate, ethyl anthranilate, ethyl-2-methyl butyrate, ethyl methylphenyl glycidate, ethyl vanillin, eugenol, flor acetate, florhydral, fructone, frutene, heliotropin, keone, indole, iso cyclo citral, isoeugenol, lyral, methyl heptine carbonate, linalool, methyl anthranilate, methyl dihydrojasmonate, methyl isobutenyl tetrahydropyran, methyl beta naphthyl ketone, beta naphthol methyl ether, nerol, para-anisic aldehyde, para hydroxy phenyl butanone, phenyl acetaldehyde, vanillin, and mixtures thereof. Use of low odor detection threshold perfume ingredients minimizes the level of organic material that is released into the atmosphere.

In order to provide compatibility with the cyclodextrin, the perfume ingredients which are hydrophobic, are preferably in a stable emulsion/dispersion. The particles of the emulsion/dispersion are preferably at least 0.01 micron in diameter, more preferably at least 0.05 micron in diameter. The emulsion is formed first and stabilized before the cyclodextrin is added. The preferred stabilizers are the siloxane surfactants described hereinafter; polymers containing both hydrophobic and hydrophilic portions; and cationic fabric softening actives in the form of stable vesicles in the desired particle size range. Thus, the composition comprises a stable hydrophobic perfume suspension (emulsion/dispersion) having a particle size of at least 0.01 micron, preferably at least 0.05 micron in diameter.

Perfume stabilizers include the siloxane surfactants described in detail as (F) (b), below,and the block copolymers described in detail as (F) (a) below, and other cyclodextrin-compatible surfactants described in (F) below. These stabilizers contain hydrophobic portions which preferably comprise monomers that are hydrophobic such as: poly butyl acrylate; poly acrylamide; poly butylaminoethyl methacrylate; poly octylacrylamide ; etc. and monomers that are hydrophilic, and preferably at least partially charged, such as: polyacrylate;. The molecular weight is preferably from about 1,000 to about 1,000,000, more preferably from about 5,000 to about 250,000, and even more preferably from about 10,000 to about 100,000. The ratio of hydrophilic portion to hydrophobic portion is preferably from 20/80 to about 90/10, more preferably from 30/70 to 75/25. The hydrophilic, preferably charged portion(s) of the polymer are preferably either in a terminal position or pendant on the hydrophobic portion, since the hydrophobic portion(s) are in the perfume and the hydrophilic portion(s) are in the water phase.

The fabric softener actives can also function as stabilizers for perfumes. Suitable cationic fabric softener actives are described in detail in U.S. Pat. No. : 5,747,443, Wahl et al. issued May 5, 1998; U.S. Pat. No. 5,830,845, Trinh et al. issued Nov. 3, 1998; U.S. Pat. No. 5,759,990, Wahl et al. issued Jun. 2, 1998; U.S. Pat. No. 5,686,376, Rusche et al. issued Nov. 11, 1997; U.S. Pat. No. 5,500,138, Bacon et al., issued Mar. 19, 1996; U.S. Pat. No. 5,545,340, Wahl et al., issued Aug. 13, 1996; U.S. Pat. No. 5,804,219, Trinh et al. issued Sep. 8, 1998; and U.S. Pat. No. 4,661,269, Trinh et al., issued Apr. 28, 1987, all of said patents being incorporated herein by reference. The softener actives are formed into a dispersion with the perfume before the cyclodextrin is added with the bulk of the water.

(F) Cyclodextrin-Compatible Surfactant

The optional, but preferred, cyclodextrin-compatible surfactant (F), provides a low surface tension that permits the composition to spread readily and more uniformly on hydrophobic surfaces like polyester and nylon. It has been found that the aqueous solution, without such a surfactant will not spread satisfactorily. Furthermore, the composition containing a cyclodextrin-compatible surfactant can penetrate hydrophobic, oily soil better for improved malodor control. Surprisingly, the combination of cyclodextrin compatible surfactant and cyclodextrin significantly boosts the cleaning performance of powder or liquid detergent on greasy stains as well. The composition containing a cyclodextrin-compatible surfactant can also provide improved "in-wear" electrostatic control. For concentrated compositions, the surfactant facilitates the dispersion of many actives such as antimicrobial actives and perfumes in the concentrated aqueous compositions.

When cyclodextrin is present, the surfactant for use in providing the required low surface tension in the composition of the present invention should be cyclodextrin-compatible, that is it should not substantially form a complex with the cyclodextrin so as to diminish performance of the cyclodextrin and/or the surfactant. Complex formation diminishes both the ability of the cyclodextrin to absorb odors and the ability of the surfactant to lower the surface tension of the aqueous composition.

Suitable cyclodextrin-compatible surfactants can be readily identified by the absence of effect of cyclodextrin on the surface tension provided by the surfactant. This is achieved by determining the surface tension (in dyne/cm) of aqueous solutions of the surfactant in the presence and in the absence of about 1% of a specific cyclodextrin in the solutions. The aqueous solutions contain surfactant at concentrations of approximately 0.5%, 0.1%, 0.01%, and 0.005%. The cyclodextrin can affect the surface activity of a surfactant by elevating the surface tension of the surfactant solution. If the surface tension at a given concentration in water differs by more than about 10% from the surface tension of the same surfactant in the 1% solution of the cyclodextrin, that is an indication of a strong interaction between the surfactant and the cyclodextrin. The preferred surfactants herein should have a surface tension in an aqueous solution that is different (lower) by less than about 10%, preferably less than about 5%, and more preferably less than about 1% from that of the same concentration solution containing 1% cyclodextrin.

(a) Block Copolymers

Nonlimiting examples of cyclodextrin-compatible nonionic surfactants include block copolymers of ethylene oxide and propylene oxide. Suitable block polyoxyethylene-polyoxypropylene polymeric surfactants, that are compatible with most cyclodextrins, include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as $C_{12-18}$ aliphatic alcohols, are not generally compatible with the cyclodextrin. Certain of the block polymer surfactant compounds designated Pluronic® and Tetronic® by the BASF-Wyandotte Corp., Wyandotte, Mich., are readily available.

Nonlimiting examples of cyclodextrin-compatible surfactants of this type include:

Pluronic Surfactants with the general formula $H(EO)_n(PO)_m(EO)_nH$, wherein EO is an ethylene oxide group, PO is a propylene oxide group, and n and m are numbers that indicate the average number of the groups in the surfactants. Typical examples of cyclodextrin-compatible Pluronic surfactants are:

| Name  | Average MW | Average n | Average m |
|-------|------------|-----------|-----------|
| L-101 | 3,800      | 4         | 59        |
| L-81  | 2,750      | 3         | 42        |
| L-44  | 2,200      | 10        | 23        |
| L-43  | 1,850      | 6         | 22        |
| F-38  | 4,700      | 43        | 16        |
| P-84  | 4,200      | 19        | 43,       | and mixtures thereof.

Tetronic Surfactants with the general formula:

wherein EO, PO, n, and m have the same meanings as above. Typical examples of cyclodextrin-compatible Tetronic surfactants are:

| Name | Average MW | Average n | Average m |
|------|------------|-----------|-----------|
| 901  | 4,700      | 3         | 18        |
| 908  | 25,000     | 114       | 22,       | and mixtures thereof.

"Reverse" Pluronic and Tetronic surfactants have the following general formulas:

Reverse Pluronic Surfactants $H(PO)_m(EO)_n(PO)_mH$

Reverse Tetronic Surfactants

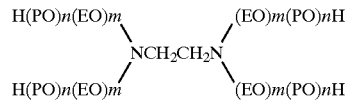

wherein EO, PO, n, and m have the same meanings as above. Typical examples of cyclodextrin-compatible Reverse Pluronic and Reverse Tetronic surfactants are:

Reverse Pluronic surfactants:

| Name  | Average MW | Average n | Average m |
|-------|------------|-----------|-----------|
| 10 R5 | 1,950      | 8         | 22        |
| 25 R1 | 2,700      | 21        | 6         |

Reverse Tetronic surfactants

| Name   | Average MW | Average n | Average m |
|--------|------------|-----------|-----------|
| 130 R2 | 7,740      | 9         | 26        |
| 70 R2  | 3,870      | 4         | 13        | and mixtures thereof.

(b) Siloxane Surfactants

A preferred class of cyclodextrin-compatible nonionic surfactants are the polyalkyleneoxide polysiloxanes having a dimethyl polysiloxane hydrophobic moiety and one or more hydrophilic polyalkylene side chains and have the general formula:

$$R^1—(CH_3)_2SiO—[(CH_3)_2SiO_a—[(CH_3)(R^1)SiO]_b—Si(CH_3)_2—R_1$$

wherein a+b are from about 1 to about 50, preferably from about 3 to about 30, more preferably from about 10 to about 25, and each $R^1$ is the same or different and is selected from the group consisting of methyl and a poly(ethyleneoxide/propyleneoxide) copolymer group having the general formula:

$$—(CH_2)_nO(C_2H_4O)_c(C_3H_6O)_dR^2$$

with at least one $R^1$ being a poly(ethyleneoxide/propyleneoxide) copolymer group, and wherein n is 3 or 4, preferably 3; total c (for all polyalkyleneoxy side groups) has a value of from 1 to about 100, preferably from about 6 to about 100; total d is from 0 to about 14, preferably from 0 to about 3; and more preferably d is 0; total c+d has a value of from about 5 to about 150, preferably from about 9 to about 100 and each $R^2$ is the same or different and is selected from the group consisting of hydrogen, an alkyl having 1 to 4 carbon atoms, and an acetyl group, preferably hydrogen and methyl group.

Examples of this type of surfactants are the Silwet® surfactants which are available OSi Specialties, Inc., Danbury, Connecticut. Representative Silwet surfactants are as follows.

| Name | Average MW | Average a + b | Average total c |
|---|---|---|---|
| L-7608 | 600 | 1 | 9 |
| L-7607 | 1,000 | 2 | 17 |
| L-77 | 600 | 1 | 9 |
| L-7605 | 6,000 | 20 | 99 |
| L-7604 | 4,000 | 21 | 53 |
| L-7600 | 4,000 | 11 | 68 |
| L-7657 | 5,000 | 20 | 76 |
| L-7602 | 3,000 | 20 | 29 |

The molecular weight of the polyalkyleneoxy group ($R^1$) is less than or equal to about 10,000. Preferably, the molecular weight of the polyalkyleneoxy group is less than or equal to about 8,000, and most preferably ranges from about 300 to about 5,000. Thus, the values of c and d can be those numbers which provide molecular weights within these ranges. However, the number of ethyleneoxy units ($-C_2H_4O$) in the polyether chain ($R^1$) must be sufficient to render the polyalkyleneoxide polysiloxane water dispersible or water soluble. If propyleneoxy groups are present in the polyalkylenoxy chain, they can be distributed randomly in the chain or exist as blocks. Preferred Silwet surfactants are L-7600, L-7602, L-7604, L-7605, L-7657, and mixtures thereof. Besides surface activity, polyalkyleneoxide polysiloxane surfactants can also provide other benefits, such as antistatic benefits, lubricity and softness to fabrics.

The preparation of polyalkyleneoxide polysiloxanes is well known in the art. Polyalkyleneoxide polysiloxanes of the present invention can be prepared according to the procedure set forth in U.S. Pat. No. 3,299,112, incorporated herein by reference. Typically, polyalkyleneoxide polysiloxanes of the surfactant blend of the present invention are readily prepared by an addition reaction between a hydrosiloxane (i.e., a siloxane containing silicon-bonded hydrogen) and an alkenyl ether (e.g., a vinyl, allyl, or methallyl ether) of an alkoxy or hydroxy end-blocked polyalkylene oxide). The reaction conditions employed in addition reactions of this type are well known in the art and in general involve heating the reactants (e.g., at a temperature of from about 85° C. to 110° C.) in the presence of a platinum catalyst (e.g., chloroplatinic acid) and a solvent (e.g., toluene).

(c) Anionic Surfactants

Nonlimiting examples of cyclodextrin-compatible anionic surfactants are the alkyldiphenyl oxide disulfonate, having the general formula:

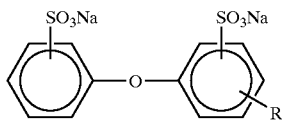

wherein R is an alkyl group. Examples of this type of surfactants are available from the Dow Chemical Company under the trade name Dowfax® wherein R is a linear or branched $C_6$–$C_{16}$ alkyl group. An example of these cyclodextrin-compatible anionic surfactant is Dowfax 3B2 with R being approximately a linear $C_{10}$ group. These anionic surfactants are preferably not used when the antimicrobial active or preservative, etc., is cationic to minimize the interaction with the cationic actives, since the effect of both surfactant and active are diminished.

(d) Castor Oil Surfactants

The cyclodextrin-compatible surfactants useful in the present invention to form molecular aggregates, such as micelles or vesicles, with the cyclodextrin-incompatible materials of the present invention further include polyoxyethylene castor oil ethers or polyoxyethylene hardened castor oil ethers or mixtures thereof, which are either partially or fully hydrogenated. These ethoxylates have the following general formulae:

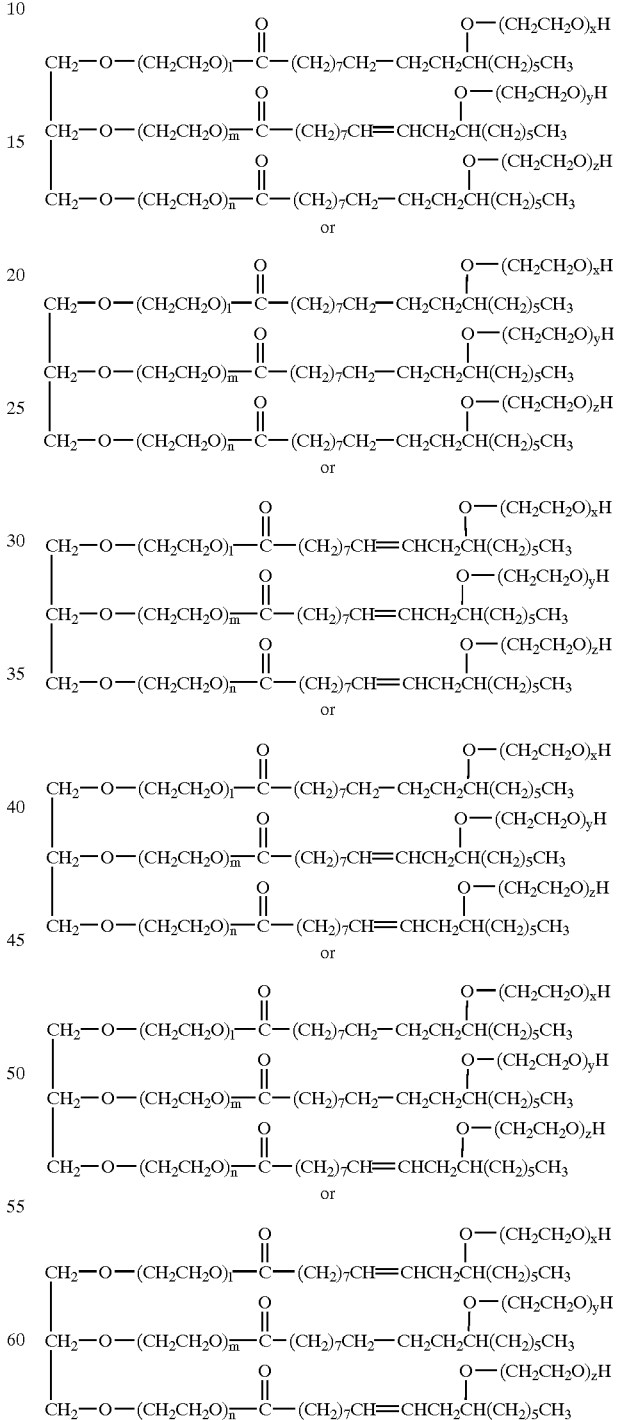

These ethoxylates can be used alone or in any mixture thereof. The average ethylene oxide addition mole number (i.e., l+m+n+x+y+z in the above formula) of these ethoxylates is generally from about 7 to about 100, and preferably from about 20 to about 80. Castor oil surfactants are commerically available from Nikko under the trade names HCO 40 and HCO 60 and from BASF under the trade names Cremphor™ RH 40, RH 60, and CO 60.

(e) Sorbitan Ester Surfactants

The sorbitan esters of long-chain fatty acids usable as cyclodextrin-compatible surfactants to form molecular aggregates with cyclodextrin-incompatible materials of the present invention include those having long-chain fatty acid residues with 14 to 18 carbon atoms, desirably 16 to 18 carbon atoms. Furthermore, the esterification degree of the sorbitan polyesters of long-chain fatty acids is desirably 2.5 to 3.5, especially 2.8 to 3.2. Typical examples of these sorbitan polyesters of long-chain fatty acids are sorbitan tripalmitate, sorbitan trioleate, and sorbitan tallow fatty acid triesters.

Other suitable sorbitan ester surfactants include sorbitan fatty acid esters, particularly the mono- and tri-esters of the formula:

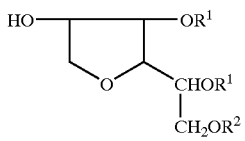

wherein $R^1$ is H or

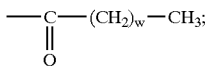

and $R^2$ is

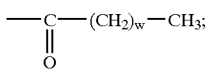

and w is from about 10 to about 16.

Further suitable sorbitan ester surfactants include polyethoxylated sorbitan fatty acid esters, particularly those of the formula:

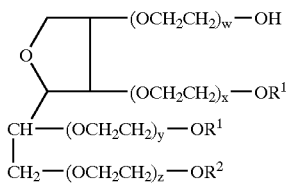

wherein $R^1$ is H or

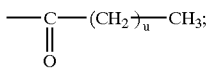

and $R^2$ is

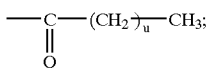

u is from about 10 to about 16 and average (w+x+y+z) is from about 2 to about 20. Preferably, u is 16 and average (w+x+y+z) is from about 2 to about 4.

(f) Polyethoxylated Fatty Alcohol Surfactants

Cyclodextrin-compatible surfactants further include polyethoxylated fatty alcohol surfactants having the formula:

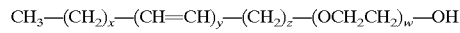

wherein w is from about 0 to about 100, preferably from about 0 to about 80; y is 0 or 1; x is from about 1 to about 10; z is from about 1 to about 10; x+z+y=11 to 25, preferably 11 to 23.

Branched (polyethoxylated) fatty alcohols having the following formula are also suitable as cyclodextrin-compatible surfactants in the present compositions:

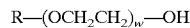

wherein R is a branched alkyl group of from about 10 to about 26 carbon atoms and w is as specified above.

(g) Glycerol Mono-Fatty Acid Ester Surfactants

Further cyclodextrin-compatible surfactants include glycerol mono-fatty acid esters, particularly glycerol monostearate, oleate, palmitate or laurate.

(h) Polyethylene Glycol Fatty Acid Ester Surfactants

Fatty acid esters of polyethylene glycol, particularly those of the following formula, are cyclodextrin-compatible surfactants useful herein:

-or-

wherein $R^1$ is a stearoyl, lauroyl, oleoyl or palmitoyl residue; w is from about 2 to about 20, preferably from about 2 to about 8.

(i) Fluorocarbon Surfactants

Further cyclodextrin-compatible surfactants useful in the present compositions include fluorocarbon surfactants. Fluorocarbon surfactants are a class of surfactants wherein the hydrophobic part of the amphiphile comprises at least in part some portion of a carbon-based linear or cyclic moiety having fluorines attached to the carbon where typically hydrogens would be attached to the carbons together with a hydrophilic head group. Some typical nonlimiting fluorocarbon surfactants include fluorinated alkyl polyoxyalkylene, and fluorinated alkyl esters as well as ionic surfactants. Representative structures for these compounds are given below:

(1) $R_fR(R_1O)_xR_2$
(2) $R_fR-OC(O)R_3$
(3) $R_fR-Y-Z$
(4) $R_fRZ$ wherein $R_f$ contains from about 6 to about 18 carbons each having from about 0 to about 3 fluorines attached. R is either an alkyl or alkylene oxide group which, when present, has from about 1 to about 10 carbons and $R_1$ represents an alkylene radical having from about 1 to about 4 carbons. $R_2$ is either a hydrogen or a small alkyl capping group having from about 1 to about 3 carbons. $R_3$ represents a hydrocarbon moiety comprising from about 2 to about 22 including the carbon on the ester group. This hydrocarbon can be linear, branched or cyclic saturated or unsaturated and contained moieties based on oxygen, nitrogen, and sulfur including, but not limited to ethers, alcohols, esters, carboxylates, amides, amines, thio-esters, and thiols; these oxygen, nitrogen, and sulfur moieties can either interrupt the hydrocabon chain or be pendant on the hydrocarbon chain.

In structure 3, Y represents a hydrocarbon group that can be an alkyl, pyridine group, amidopropyl, etc. that acts as a linking group between the fluorinated chain and the hydrophilic head group. In structures 3 and 4, Z represents a cationic, anionic, and amphoteric hydrophilic head groups including, but not limited to carboxylates, sulfates, sulfonates, quaternary ammonium groups, and betaines. Nonlimiting commercially available examples of these structures include Zonyl® 9075, FSO, FSN, FS-300, FS-310, FSN-100, FSO-100, FTS, TBC from DuPont and Fluorad™ surfactants FC-430, FC-43 1, FC-740, FC-99, FC-120, FC-754, FC170C, and FC-171 from the 3M™ company in St. Paul, Minn.

The cyclodextrin-compatible surfactants described above are either weakly interactive with cyclodextrin (less than 5% elevation in surface tension), or non-interactive (less than 1% elevation in surface tension). Normal surfactants like sodium dodecyl sulfate and dodecanolpoly(6)ethoxylate are strongly interactive, with more than a 10% elevation in surface tension in the presence of a typical cyclodextrin like hydroxypropyl beta-cyclodextrin and methylated beta-cyclodextrin.

Typical levels of cyclodextrin-compatible surfactants in usage compositions are from about 0.01% to about 2%, preferably from about 0.03% to about 0.6%, more preferably from about 0.05% to about 0.3%, by weight of the composition. Typical levels of cyclodextrin-compatible surfactants in concentrated compositions are from about 0.1% to about 8%, preferably from about 0.2% to about 4%, more preferably from about 0.3% to about 3%, by weight of the concentrated composition.

(G) Soil Suspending Agent

The compositions of the present invention may also optionally comprise at least about 0.01%, preferably at least about 0.05%, and to about 10%, preferably to about 5% by weight, of a soil suspending agent such as a water-soluble substituted or unsubstituted, modified or unmodified polyalkyleneimine soil suspending agent, said soil suspending agent comprising a polyamine backbone, preferably said backbone having a molecular weight of from about 100 to about 5000 daltons having the formula:

said backbones prior to subsequent modification, comprise primary, secondary and tertiary amine nitrogens connected by R "linking" units. The backbones are comprised of essentially three types of units, which may be randomly distributed along the chain.

The units which make up the polyalkyleneimine backbones are primary amine units having the formula:

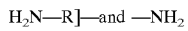

which terminate the main backbone and any branching chains, secondary amine units having the formula:

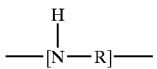

and which, after modification, have their hydrogen atoms preferably substituted by alkyleneoxy units as described herein below, and tertiary amine units having the formula:

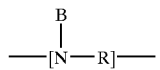

which are the branching points of the main and secondary backbone chains, B representing a continuation of the chain structure by branching. The tertiary units have no replaceable hydrogen atom and are therefore not modified by substitution with an alkyleneoxy unit.

R is $C_2$–$C_{12}$ alkylene, $C_3$–$C_6$ branched alkylene, and mixtures thereof, preferred branched alkylene is 1,2-propylene; most preferred R is ethylene. The preferred polyalkyleneimines of the present invention have backbones which comprise the same R unit, for example, all units are ethylene. Most preferred backbone comprises R groups which are all ethylene units.

The polyalkyleneimines of the present invention are modified by substitution of each N—H unit hydrogen with an alkyleneoxy unit having the formula:

wherein $R^1$ is $C_2$–$C_{12}$ alkylene, preferably ethylene, 1,2-propylene, 1,3-propylene, 1,2-butylene, 1,4-butylene, and mixtures thereof, more preferably ethylene and 1,2-propylene, most preferably ethylene. $R^2$ is hydrogen, $C_1$–$C_4$ alkyl, and mixtures thereof, preferably hydrogen or methyl, more preferably hydrogen.

The molecular weight of the backbone prior to modification as well as the value of the index n is largely dependent upon the benefits and properties which the formulator wishes to provide. For example, U.S. Pat. No. 5,565,145 Watson et al., issued October 15, 1996, discloses a preferred polyamine having a backbone $M_w$ of 1800 daltons and about 7 ethyleneoxy units per nitrogen as a modified polyalkyleneimine suitable for use as hydrophobic, inter alia, soot, grime, soil suspending agent. The substantivity of alkyleneoxy substituted polyamines toward fabric surface can be adjusted by the formulator to meet the needs of the specific embodiment.

U.S. Pat. No. 4,891,160 Vander Meer, issued Jan. 2, 1990; U.S. Pat. No. 4,597,898, Vander Meer, issued Jul. 1, 1986 describe a polyamine having a backbone $M_w$ of 189 daltons and an average of from about 15 to 18 ethyleneoxy units per nitrogen as a suitable soil suspending agent for hydrophilic, inter alia, clay soils.

A further description of polyamine soil suspending agents suitable for use in the present invention is found in; U.S. patent application Ser. No. 09/103,135; U.S. Pat. No. 6,004, 922 Watson et al., issued Dec. 21, 1999; and U.S. Pat. No. 4,664,848 Oh et al., issued May 12, 1987 all of which are included herein by reference.

The polyamines of the present invention can be prepared, for example, by polymerizing ethyleneimine in the presence of a catalyst such as carbon dioxide, sodium bisulfite, sulfuric acid, hydrogen peroxide, hydrochloric acid, acetic acid, etc. Specific methods for preparing these polyamine backbones are disclosed in U.S. Pat. No. 2,182,306, Ulrich et al., issued Dec. 5, 1939; U.S. Pat. No. 3,033,746, Mayle et al., issued May 8, 1962; U.S. Pat. No. 2,208,095, Esselmann et al., issued Jul. 16, 1940; U.S. Pat. No. 2,806,839, Crowther, issued Sep. 17, 1957; and U.S. Pat. No. 2,553, 696, Wilson, issued May 21, 1951; all herein incorporated by reference.

(H) Cyclodextrin-Compatible Antimicrobial Active

The solubilized, water-soluble antimicrobial active, (H), is useful in providing protection against organisms that become attached to the treated material. The antimicrobial should be cyclodextrin-compatible, e.g., not substantially forming complexes with the cyclodextrin in the odor absorbing composition. The free, uncomplexed antimicrobial, e.g., antibacterial, active provides an optimum antibacterial performance.

Sanitization of fabrics can be achieved by the compositions of the present invention containing, antimicrobial materials, e.g., antibacterial halogenated compounds, quaternary compounds, and phenolic compounds.

Biguanides. Some of the more robust cyclodextrin-compatible antimicrobial halogenated compounds which can function as disinfectants/sanitizers as well as finish product preservatives (vide infra), and are useful in the compositions of the present invention include 1,1'-hexamethylene bis(5-(p-chlorophenyl)biguanide), commonly known as chlorhexidine, and its salts, e.g., with hydrochloric, acetic and gluconic acids. The digluconate salt is highly water-soluble, about 70% in water, and the diacetate salt has a solubility of about 1.8% in water. When chlorhexidine is used as a sanitizer in the present invention it is typically present at a level of from about 0.001% to about 0.4%, preferably from about 0.002% to about 0.3%, and more preferably from about 0.05% to about 0.2%, by weight of the usage composition. In some cases, a level of from about 1% to about 2% may be needed for virucidal activity.

Other useful biguanide compounds include Cosmoci® CQ®, Vantocil® IB, including poly (hexamethylene biguanide) hydrochloride. Other useful cationic antimicrobial agents include the bis-biguanide alkanes. Usable water soluble salts of the above are chlorides, bromides, sulfates, alkyl sulfonates such as methyl sulfonate and ethyl sulfonate, phenylsulfonates such as p-methylphenyl sulfonates, nitrates, acetates, gluconates, and the like.

Examples of suitable bis biguanide compounds are chlorhexidine; 1,6-bis-(2-ethylhexylbiguanidohexane) dihydrochloride; 1,6-di-($N_1$,$N_1$'-phenyldiguanido-$N_5$,$N_5$')-hexane tetrahydrochloride; 1,6-di-($N_1$,$N_1$'-phenyl-$N_1$,$N_1$'-methyldiguanido-$N_5$,$N_5$')-hexane dihydrochloride; 1,6-di ($N_1$,$N_1$'-o-chlorophenyldiguanido-$N_5$,$N_5$')-hexane dihydrochloride; 1,6-di($N_1$,$N_1$'-2,6-dichlorophenyldiguanido-$N_5$,$N_5$')hexane dihydrochloride; 1,6-di[$N_1$,$N_1$'-.beta.-(p-methoxyphenyl) diguanido-$N_5$,$N_5$']-hexane dihydrochloride; 1,6-di($N_1$,$N_1$'-.alpha.-methyl-.beta.-phenyldiguanido-$N_5$,$N_5$')-hexane dihydrochloride; 1,6-di($N_1$,$N_1$'-p-nitrophenyldiguanido-$N_5$,$N_5$')hexane dihydrochloride;.omega.:.omega.'-di-($N_1$,$N_1$'-phenyldiguanido-$N_5$,$N_5$')-di-n-propylether dihydrochloride;.omega:omega'-di($N_1$,$N_1$'-p-chlorophenyldiguanido-$N_5$,$N_5$')-di-n-propylether tetrahydrochloride; 1,6-di($N_1$,$N_1$'-2,4-dichlorophenyldiguanido-$N_5$,$N_5$')hexane tetrahydrochloride; 1,6-di($N_1$,$N_1$'-p-methylphenyldiguanido-$N_5$,$N_5$')hexane dihydrochloride; 1,6-di($N_1$,$N_1$'-2,4,5-trichlorophenyldiguanido-$N_5$,$N_5$') hexane tetrahydrochloride; 1,6-di[$N_1$,$N_1$'-.alpha.-(p-chlorophenyl) ethyldiguanido-$N_5$,$N_5$'] hexane dihydrochloride;.omega.:.omega.'di($N_1$,$N_1$-p-chlorophenyldiguanido-$N_5$,$N_5$')m-xylene dihydrochloride; 1,12-di($N_1$,$N_1$'-p-chlorophenyldiguanido-$N_5$,$N_5$') dodecane dihydrochloride; 1,10-di($N_1$,$N_1$'-phenyldiguanido-$N_5$,$N_5$')-decane tetrahydrochloride; 1,12-di($N_1$,$N_1$'-phenyldiguanido-$N_5$,$N_5$') dodecane tetrahydrochloride; 1,6-di($N_1$,$N_1$'-o-chlorophenyldiguanido-$N_5$,$N_5$') hexane dihydrochloride; 1,6-di($N_1$,$N_1$'-p-chlorophenyldiguanido-$N_5$,$N_5$')-hexane tetrahydrochloride; ethylene bis (1-tolyl biguanide); ethylene bis(p-tolyl biguanide); ethylene bis(3,5-dimethylphenyl biguanide); ethylene bis(p-tert-amylphenyl biguanide); ethylene bis(nonylphenyl biguanide); ethylene bis (phenyl biguanide); ethylene bis(N-butylphenyl biguanide); ethylene bis(2,5-diethoxyphenyl biguanide); ethylene bis(2,4-dimethylphenyl biguanide); ethylene bis(o-diphenylbiguanide); ethylene bis(mixed amyl naphthyl biguanide); N-butyl ethylene bis (phenylbiguanide); trimethylene bis(o-tolyl biguanide); N-butyl trimethylene bis(phenyl biguanide); and the corresponding pharmaceutically acceptable salts of all of the above such as the acetates; gluconates; hydrochlorides; hydrobromides; citrates; bisulfites; fluorides; polymaleates; N-coconutalkylsarcosinates; phosphites; hypophosphites; perfluorooctanoates; silicates; sorbates; salicylates; maleates; tartrates; fumarates; ethylenediaminetetraacetates; iminodiacetates; cinnamates; thiocyanates; arginates; pyromellitates; tetracarboxybutyrates; benzoates; glutarates; monofluorophosphates; and perfluoropropionates, and mixtures thereof. Preferred antimicrobials from this group are 1,6-di-($N_1$,$N_1$'-phenyldiguanido-$N_5$,$N_5$')-hexane tetrahydrochloride; 1,6-di($N_1$,$N_1$'-o-chlorophenyldiguanido-$N_5$,$N_5$')-hexane dihydrochloride; 1,6-di($N_1$,$N_1$'-2,6-dichlorophenyldiguanido-$N_5$,$N_5$')hexane dihydrochloride; 1,6-di($N_1$,$N_1$'-2,4-dichlorophenyldiguanido-$N_5$,$N_5$')hexane tetrahydrochloride; 1,6-di[$N_1$,$N_1$'-.alpha.-(p-chlorophenyl) ethyldiguanido-$N_5$,$N_5$'] hexane dihydrochloride;.omega.:.omega.'di($N_1$, $N_1$'-p-chlorophenyldiguanido-$N_5$,$N_5$')m-xylene dihydrochloride; 1,12-di($N_1$,$N_1$'-p-chlorophenyldiguanido-$N_5$,$N_5$') dodecane dihydrochloride; 1,6-di($N_1$,$N_1$'-o-chlorophenyldiguanido-$N_5$,$N_5$') hexane dihydrochloride; 1,6-di($N_1$,$N_1$'-p-chlorophenyldiguanido-$N_5$,$N_5$')-hexane tetrahydrochloride; and mixtures thereof; more preferably, 1,6-di($N_1$,$N_1$'-o-chlorophenyldiguanido-$N_5$,$N_5$')-hexane dihydrochloride; 1,6-di($N_1$,$N_1$'-2,6-dichlorophenyldiguanido-$N_5$,$N_5$')hexane dihydrochloride; 1,6-di($N_1$,$N_1$'-2,4-dichlorophenyldiguanido-$N_5$,$N_5$')hexane tetrahydrochloride; 1,6-di[$N_1$,$N_1$'-.alpha.-(p-chlorophenyl) ethyldiguanido-$N_5$,$N_5$']hexane dihydrochloride;.omega.:.omega.'di($N_1$, $N_1$'-p-chlorophenyldiguanido-$N_5$,$N_5$')m-xylene dihydrochloride; 1,12-di($N_1$,$N_1$'-p-chlorophenyldiguanido-$N_5$,$N_5$') dodecane dihydrochloride; 1,6-di($N_1$,$N_1$'-o-chlorophenyldiguanido-$N_5$,$N_5$') hexane dihydrochloride; 1,6-di($N_1$,$N_1$'-p-chlorophenyldiguanido-$N_5$,$N_5$')-hexane tetrahydrochloride; and mixtures thereof. As stated hereinbefore, the bis biguanide of choice is chlorhexidine its salts, e.g., digluconate, dihydrochloride, diacetate, and mixtures thereof.

Quaternary Compounds. A wide range of quaternary compounds can also be used as antimicrobial actives, in conjunction with the preferred surfactants, for compositions of the present invention that do not contain cyclodextrin. Non-limiting examples of useful quaternary compounds include: (1) benzalkonium chlorides and/or substituted benzalkonium chlorides such as commercially available Barquat® (available from Lonza), Maquat® (available from Mason), Variquat® (available from Witco/Sherex), and Hyamine® (available from Lonza); (2) di($C_6$–$C_{14}$)alkyl di short chain ($C_{1-4}$ alkyl and/or hydroxyalkl) quaternary such as Bardac® products of Lonza, (3) N-(3-chloroallyl) hexaminium chlorides such as Dowicide® and Dowicil® available from Dow; (4) benzethonium chloride such as Hyamine® 1622 from Rohm & Haas; (5) methylbenzethonium chloride represented by Hyamine® 10X supplied by Rohm & Haas, (6) cetylpyridinium chloride such as Cepacol chloride available from of Merrell Labs. Examples of the preferred dialkyl quaternary compounds are di($C_8$–$C_{12}$)

dialkyl dimethyl ammonium chloride, such as didecyldimethylammonium chloride (Bardac 22), and dioctyldimethylammonium chloride (Bardac 2050). Typical concentrations for biocidal effectiveness of these quaternary compounds range from about 0.001% to about 0.8%, preferably from about 0.005% to about 0.3%, more preferably from about 0.01% to about 0.2%, and even more preferably from about 0.03% to about 0.1%, by weight of the usage composition. The corresponding concentrations for the concentrated compositions are from about 0.003% to about 2%, preferably from about 0.006% to about 1.2%, and more preferably from about 0.1% to about 0.8% by weight of the concentrated compositions.

The surfactants, when added to the antimicrobials tend to provide improved antimicrobial action. This is especially true for the siloxane surfactants, and especially when the siloxane surfactants are combined with the chlorhexidine or Bardac antimicrobial actives.

(I) Low Molecular Weight Polyols

Low molecular weight polyols with relatively high boiling points, as compared to water, such as ethylene glycol, diethylene glycol, triethylene glycol, propylene glycol, dipropylene glycol, and/or glycerine are preferred optional ingredients for improving odor control performance of the composition of the present invention. Not to be bound by theory, it is believed that the incorporation of a small amount of low molecular weight glycols into the composition of the present invention enhances the formation of the cyclodextrin inclusion complexes as the fabric dries.

It is believed that the polyols' ability to remain on the fabric for a longer period of time than water, as the fabric dries allows it to form ternary complexes with the cyclodextrin and some malodorous molecules. The addition of the glycols is believed to fill up void space in the cyclodextrin cavity that is unable to be totally filled by some malodor molecules of relatively smaller sizes. Preferably the glycol used is glycerine, ethylene glycol, propylene glycol, dipropylene glycol or mixtures thereof, more preferably ethylene glycol and propylene glycol. Cyclodextrins prepared by processes that result in a level of such polyols are highly desirable, since they can be used without removal of the polyols.

Some polyols, e.g., dipropylene glycol, are also useful to facilitate the solubilization of some perfume ingredients in the composition of the present invention.

Typically, glycol is added to the composition of the present invention at a level of from about 0.01% to about 3%, by weight of the composition, preferably from about 0.05% to about 1%, more preferably from about 0.1% to about 0.5%, by weight of the composition. The preferred weight ratio of low molecular weight polyol to cyclodextrin is from about 2:1,000 to about 20:100, more preferably from about 3:1,000 to about 15:100, even more preferably from about 5:1,000 to about 10:100, and most preferably from about 1:100 to about 7:100.

(J) Optional Aminocarboxylate Chelators

Chelators, e.g., ethylenediaminetetraacetic acid (EDTA), hydroxyethylene-diaminetriacetic acid, diethylenetriaminepentaacetic acid, and other aminocarboxylate chelators, and mixtures thereof, and their salts, and mixtures thereof, can optionally be used to increase antimicrobial and preservative effectiveness against Gram-negative bacteria, especially Pseudomonas species. Although sensitivity to EDTA and other aminocarboxylate chelators is mainly a characteristic of Pseudomonas species, other bacterial species highly susceptible to chelators include Achromobacter, Alcaligenes, Azotobacter, Escherichia, Salmonella, Spirillum, and Vibrio. Other groups of organisms also show increased sensitivities to these chelators, including fungi and yeasts. Furthermore, aminocarboxylate chelators can help, e.g., maintaining product clarity, protecting fragrance and perfume components, and preventing rancidity and off odors.

Although these aminocarboxylate chelators may not be potent biocides in their own right, they function as potentiators for improving the performance of other antimicrobials/preservatives in the compositions of the present invention. Aminocarboxylate chelators can potentiate the performance of many of the cationic, anionic, and nonionic antimicrobials/preservatives, phenolic compounds, and isothiazolinones, that are used as antimicrobials/preservatives in the composition of the present invention. Nonlimiting examples of cationic antimicrobials/preservatives potentiated by aminocarboxylate chelators in solutions are chlorhexidine salts (including digluconate, diacetate, and dihydrochloride salts), and Quaternium-15, also known as Dowicil 200, Dowicide Q, Preventol D1, benalkonium chloride, cetrimonium, myristalkonium chloride, cetylpyridinium chloride, lauryl pyridinium chloride, and the like. Nonlimiting examples of useful anionic antimicrobials/preservatives which are enhanced by aminocarboxylate chelators are sorbic acid and potassium sorbate. Nonlimiting examples of useful nonionic antimicrobials/preservatives which are potentiated by aminocarboxylate chelators are DMDM hydantoin, phenethyl alcohol, monolaurin, imidazolidinyl urea, and Bronopol (2-bromo-2-nitropropane-1,3-diol).

Examples of useful phenolic antimicrobials/preservatives potentiated by these chelators are chloroxylenol, phenol, tert-butyl hydroxyanisole, salicylic acid, resorcinol, and sodium o-phenyl phenate. Nonlimiting examples of isothiazolinone antimicrobials/preservatives which are enhanced by aminocarboxylate chelators are Kathon, Proxel and Promexal.

The optional chelators are present in the compositions of this invention at levels of, typically, from about 0.01% to about 0.3%, more preferably from about 0.02% to about 0.1%, most preferably from about 0.02% to about 0.05% by weight of the usage compositions to provide antimicrobial efficacy in this invention.

Free, uncomplexed aminocarboxylate chelators are required to potentiate the efficacy of the antimicrobials. Thus, when excess alkaline earth (especially calcium and magnesium) and transitional metals (iron, manganese, copper, and others) are present, free chelators are not available and antimicrobial potentiation is not observed. In the case where significant water hardness or transitional metals are available or where product esthetics require a specified chelator level, higher levels may be required to allow for the availability of free, uncomplexed aminocarboxylate chelators to function as antim icrobial/preservative potentiators.

(K) Metal Salts

Optionally, but highly preferred, the present invention can include metallic salts for added odor absorption and/or antimicrobial benefit for the cyclodextrin solution. The metallic salts are selected from the group consisting of copper salts, zinc salts, and mixtures thereof.

Copper salts have some antimicrobial benefits. Specifically, cupric abietate acts as a fungicide, copper acetate acts as a mildew inhibitor, cupric chloride acts as a fungicide, copper lactate acts as a fungicide, and copper sulfate acts as a germicide. Copper salts also possess some malodor control abilities. See U.S. Pat. No. 3,172,817, Leupold, et al., which discloses deodorizing compositions for treating disposable articles, comprising at least slightly water-soluble salts of acylacetone, including copper salts and zinc salts, all of said patents are incorporated herein by reference.

The preferred zinc salts possess malodor control abilities. Zinc has been used most often for its ability to ameliorate malodor, e.g., in mouth wash products, as disclosed in U.S. Pat. No. 4,325,939, issued Apr. 20, 1982 and U.S. Pat. No. 4,469,674, issued Sep. 4, 1983, to N. B. Shah, et al., all of which are incorporated herein by reference. Highly-ionized and soluble zinc salts such as zinc chloride, provide the best source of zinc ions. Zinc borate functions as a fungistat and a mildew inhibitor, zinc caprylate functions as a fungicide, zinc chloride provides antiseptic and deodorant benefits, zinc ricinoleate functions as a fungicide, zinc sulfate heptahydrate functions as a fungicide and zinc undecylenate functions as a fungistat.

Preferably the metallic salts are water-soluble zinc salts, copper salts or mixtures thereof, and more preferably zinc salts, especially $ZnCl_2$. These salts are preferably present in the present invention primarily to absorb amine and sulfur-containing compounds that have molecular sizes too small to be effectively complexed with the cyclodextrin molecules. Low molecular weight sulfur-containing materials, e.g., sulfide and mercaptans, are components of many types of malodors, e.g., food odors (garlic, onion), body/perspiration odor, breath odor, etc. Low molecular weight amines are also components of many malodors, e.g., food odors, body odors, urine, etc.

When metallic salts are added to the composition of the present invention they are typically present at a level of from about 0.1% to about 10%, preferably from about 0.2% to about 8%, more preferably from about 0.3% to about 5% by weight of the usage composition. When zinc salts are used as the metallic salt, and a clear solution is desired, it is preferable that the pH of the solution is adjusted to less than about 7, more preferably less than about 6, most preferably, less than about 5, in order to keep the solution clear.

(L) Preservative

Optionally, the composition can contain an effective amount of solubilized, water-soluble, antimicrobial preservative, preferably from about 0.0001% to about 0.5%, more preferably from about 0.0002% to about 0.2%, most preferably from about 0.0003% to about 0.1%, by weight of the composition.

Optionally, but preferably, solubilized, water-soluble, antimicrobial preservative can be added to the composition of the present invention if the antimicrobial material is not sufficient, or is not present, when cyclodextrin is present, because cyclodextrin molecules are made up of varying numbers of glucose units which can make them a prime breeding ground for certain microorganisms, especially when in aqueous compositions. This drawback can lead to the problem of storage stability of cyclodextrin solutions for any significant length of time. Contamination by certain microorganisms with subsequent microbial growth can result in an unsightly and/or malodorous solution. Because microbial growth in cyclodextrin solutions is highly objectionable when it occurs, it is highly preferable to include a solubilized, water-soluble, antimicrobial preservative, which is effective for inhibiting and/or regulating microbial growth in order to increase storage stability of the preferably clear, aqueous odor-absorbing solution containing water-soluble cyclodextrin.

Typical microorganisms that can be found in cyclodextrin supplies and whose growth can be found in the presence of cyclodextrin in aqueous cyclodextrin solutions include bacteria, e.g., *Bacillus thuringiensis* (cereus group) and *Bacillus sphaericus*; and fungi, e.g., *Aspergillus ustus*. *Bacillus sphaericus* is one of the most numerous members of Bacillus species in soils. *Aspergillus ustus* is common in grains and flours which are raw materials to produce cyclodextrins. Microorganisms such as *Escherichia coli* and *Pseudomonas aeruginosa* are found in some water sources, and can be introduced during the preparation of cyclodextrin solutions. Other Pseudomonas species, such as *P. cepacia*, are typical microbial contaminants in surfactant manufacturing facilities and may readily contaminate packed finished products. Typical other bacterial contaminants may include Burkholderia, Enterobacter and Gluconobacter species. Representative fungal species which may be associated with agricultural soils, crops and in the case of this invention, corn products such as cyclodextrins include Aspergillus. Absidia, Penicillium, Paecilomyces, and other species.

It is preferable to use a broad spectrum preservative, e.g., one that is effective on both bacteria (both gram positive and gram negative) and fungi. A limited spectrum preservative, e.g., one that is only effective on a single group of microorganisms, e.g., fungi, can be used in combination with a broad spectrum preservative or other limited spectrum preservatives with complimentary and/or supplementary activity. A mixture of broad spectrum preservatives can also be used. In some cases where a specific group of microbial contaminants is problematic (such as Gram negatives), aminocarboxylate chelators may be used alone or as potentiators in conjunction with other preservatives. These chelators which include, e.g., ethylenediam inetetraacetic acid (EDTA), hydroxyethylenediaminetriacetic acid, diethylenetriaminepentaacetic acid, and other aminocarboxylate chelators, and mixtures thereof, and their salts, and mixtures thereof, can increase preservative effectiveness against Gram-negative bacteria, especially Pseudomonas species.

Antimicrobial preservatives useful in the present invention include biocidal compounds, i.e., substances that kill microorganisms, or biostatic compounds, i.e., substances that inhibit and/or regulate the growth of microorganisms.

Preferred antimicrobial preservatives are those that are water-soluble and are effective at low levels because the organic preservatives can form inclusion complexes with the cyclodextrin molecules and compete with the malodorous molecules for the cyclodextrin cavities, thus rendering the cyclodextrins ineffective as odor controlling actives. Water-soluble preservatives useful in the present invention are those that have a solubility in water of at least about 0.3 g per 100 ml of water, i.e., greater than about 0.3% at room temperature, preferably greater than about 0.5% at room temperature. These types of preservatives have a lower affinity to the cyclodextrin cavity, at least in the aqueous phase, and are therefore more available to provide antimicrobial activity. Preservatives with a water-solubility of less than about 0.3% and a molecular structure that readily fits into the cyclodextrin cavity, have a greater tendency to form inclusion complexes with the cyclodextrin molecules, thus rendering the preservative less effective to control microbes in the cyclodextrin solution. Therefore, many well known preservatives such as short chain alkyl esters of p-hydroxybenzoic acid, commonly known as parabens; N-(4-chlorophenyl)-N'-(3,4-dichlorophenyl) urea, also known as 3,4,4'-trichlorocarbanilide or triclocarban; 2,4,4'-trichloro-2'-hydroxy diphenyl ether, commonly known as triclosan are not preferred in the present invention since they are relatively ineffective when used in conjunction with cyclodextrin.

The water-soluble antimicrobial preservative in the present invention is included at an effective amount. The term "effective amount" as herein defined means a level sufficient to prevent spoilage, or prevent growth of inadvertently added microorganisms, for a specific period of time. In other words, the preservative is not being used to kill microorganisms on the surface onto which the composition is deposited in order to eliminate odors produced by microorganisms. Instead, it is preferably being used to prevent spoilage of the cyclodextrin solution in order to increase the shelf-life of the composition. Preferred levels of preservative are from about 0.0001% to about 0.5%, more preferably from about 0.0002% to about 0.2%, most preferably from about 0.0003% to about 0.1%, by weight of the usage composition.

In order to reserve most of the cyclodextrins for odor control, the cyclodextrin to preservative molar ratio should be greater than about 5:1, preferably greater than about 10:1, more preferably greater than about 50:1, even more preferably greater than about 100:1.

The preservative can be any organic preservative material which will not cause damage to fabric appearance, e.g., discoloration, coloration, bleaching. Preferred water-soluble preservatives include organic sulfur compounds, halogenated compounds, cyclic organic nitrogen compounds, low molecular weight aldehydes, quaternary ammonium compounds, dehydroacetic acid, phenyl and phenolic compounds, and mixtures thereof.

The following are non-limiting examples of preferred water-soluble preservatives for use in the present invention.

(1). Organic Sulfur Compounds

Preferred water-soluble preservatives for use in the present invention are organic sulfur compounds. Some non-limiting examples of organic sulfur compounds suitable for use in the present invention are:

(a) 3-Isothiazolone Compounds

A preferred preservative is an antimicrobial, organic preservative containing 3-isothiazolone groups having the formula:

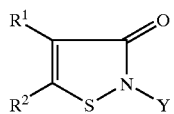

wherein

Y is an unsubstituted alkyl, alkenyl, or alkynyl group of from about 1 to about 18 carbon atoms, an unsubstituted or substituted cycloalkyl group having from about a 3 to about a 6 carbon ring and up to 12 carbon atoms, an unsubstituted or substituted aralkyl group of up to about 10 carbon atoms, or an unsubstituted or substituted aryl group of up to about 10 carbon atoms;

$R^1$ is hydrogen, halogen, or a ($C_1$–$C_4$) alkyl group; and $R^2$ is hydrogen, halogen, or a ($C_1$–$C_4$) alkyl group.

Preferably, when Y is methyl or ethyl, $R^1$ and $R^2$ should not both be hydrogen. Salts of these compounds formed by reacting the compound with acids such as hydrochloric, nitric, sulfuric, etc. are also suitable.

This class of compounds is disclosed in U.S. Pat. No. 4,265,899, Lewis et al., issued May 5, 1981, and incorporated herein by reference. Examples of said compounds are: 5-chloro-2-methyl-4-isothiazolin-3-one; 2-n-butyl-3-isothiazolone; 2-benzyl-3-isothiazolone; 2-phenyl-3-isothiazolone, 2-methyl-4,5-dichloroisothiazolone; ; 5-chloro-2-methyl-3-isothiazolone; 2-methyl-4-isothiazolin-3-one; and mixtures thereof. A preferred preservative is a water-soluble mixture of 5-chloro-2-methyl-4-isothiazolin-3-one and 2-methyl-4-isothiazolin-3-one, more preferably a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Company.

When Kathon® is used as the preservative in the present invention it is present at a level of from about 0.0001% to about 0.01%, preferably from about 0.0002% to about 0.005%, more preferably from about 0.0003% to about 0.003%, most preferably from about 0.0004% to about 0.002%, by weight of the composition.

Other isothiazolins include 1,2-benzisothiazolin-3-one, available under the trade name Proxel® products; and 2-methyl-4,5-trimethylene-4-isothiazolin-3-one, available under the trade name Promexal®. Both Proxel and Promexal are available from Zeneca. They have stability over a wide pH range (i.e., 4–12). Neither contain active halogen and are not formaldehyde releasing preservatives. Both Proxel and Promexal are effective against typical Gram negative and positive bacteria, fungi and yeasts when used at a level from about 0.001% to about 0.5%, preferably from about 0.005% to about 0.05%, and most preferably from about 0.01% to about 0.02% by weight of the usage composition.

(b) Sodium Pyrithione

Another preferred organic sulfur preservative is sodium pyrithione, with water solubility of about 50%. When sodium pyrithione is used as the preservative in the present invention it is typically present at a level of from about 0.0001% to about 0.01%, preferably from about 0.0002% to about 0.005%, more preferably from about 0.0003% to about 0.003%, by weight of the usage composition.

Mixtures of the preferred organic sulfur compounds can also be used as the preservative in the present invention.

(2). Halogenated Compounds

Preferred preservatives for use in the present invention are halogenated compounds. Some non-limiting examples of halogenated compounds suitable for use in the present invention are:

5-bromo-5-nitro-1,3-dioxane, available under the trade name Bronidox L® from Henkel. Bronidox L® has a solubility of about 0.46% in water. When Bronidox is used as the preservative in the present invention it is typically present at a level of from about 0.0005% to about 0.02%, preferably from about 0.001% to about 0.01%, by weight of the usage composition;

2-bromo-2-nitropropane-1,3-diol, available under the trade name Bronopol® from Inolex can be used as the preservative in the present invention. Bronopol has a solubility of about 25% in water. When Bronopol is used as the preservative in the present invention it is typically present at a level of from about 0.002% to about 0.1%, preferably from about 0.005% to about 0.05%, by weight of the usage composition;

1,1'-hexamethylene bis(5-(p-chlorophenyl)biguanide), commonly known as chlorhexidine, and its salts, e.g., with acetic and gluconic acids can be used as a preservative in the present invention. The digluconate salt is highly water-soluble, about 70% in water, and the diacetate salt has a solubility of about 1.8% in water. When chlorhexidine is used as the preservative in the present invention it is typically present at a level of from about 0.0001% to about 0.04%, preferably from about 0.0005% to about 0.01%, by weight of the usage composition.

1,1,1-Trichloro-2-methylpropan-2-ol, commonly known as chlorobutanol, with water solubility of about 0.8%; a typical effective level of chlorobutanol is from about 0.1% to about 0.5%, by weight of the usage composition.

4,4'-(Trimethylenedioxy)bis-(3-bromobenzamidine) diisethionate, or dibromopropamidine, with water solubility of about 50%; when dibromopropamidine is used as the preservative in the present invention it is typically present at a level of from about 0.0001% to about 0.05%, preferably from about 0.0005% to about 0.01% by weight of the usage composition.

Mixtures of the preferred halogenated compounds can also be used as the preservative in the present invention.

(3). Cyclic Organic Nitrogen Compounds

Preferred water-soluble preservatives for use in the present invention are cyclic organic nitrogen compounds. Some non-limiting examples of cyclic organic nitrogen compounds suitable for use in the present invention are:

(a) Imidazolidinedione Compounds

Preferred preservatives for use in the present invention are imidazolidione compounds. Some non-limiting examples of imidazolidinedione compounds suitable for use in the present invention are:

1,3-bis(hydroxymethyl)-5,5-dimethyl-2,4-imidazolidine-dione, commonly known as dimethyloldimethylhydantoin, or DMDM hydantoin, available as, e.g., Glydant® from Lonza. DMDM hydantoin has a water solubility of more than 50% in water, and is mainly effective on bacteria. When DMDM hydantoin is used, it is preferable that it be used in combination with a broad spectrum preservative such as Kathon CG®, or formaldehyde. A preferred mixture is about a 95:5 DMDM hydantoin to 3-butyl-2-iodopropynylcarbamate mixture, available under the trade name Glydant Plus® from Lonza. When Glydant Plus® is used as the preservative in the present invention, it is typically present at a level of from about 0.005% to about 0.2% by weight of the usage composition;

N-[1,3-bis(hydroxymethyl)2,5-dioxo-4-imidazol idinyl]-N,N'-bis(hydroxymethyl) urea, commonly known as diazolidinyl urea, available under the trade name Germall II® from Sutton Laboratories, Inc. (Sutton) can be used as the preservative in the present invention. When Germall II® is used as the preservative in the present invention, it is typically present at a level of from about 0.01% to about 0.1% by weight of the usage composition;

N,N"-methylenebis {N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from (Sutton) can be used as the preservative in the present invention. When imidazolidinyl urea is used as the preservative, it is typically present at a level of from about 0.05% to about 0.2%, by weight of the usage composition.

Mixtures of the preferred imidazolidinedione compounds can also be used as the preservative in the present invention.

(b) Polymethoxy Bicyclic Oxazolidine

Another preferred water-soluble cyclic organic nitrogen preservative is polymethoxy bicyclic oxazolidine, having the general formula:

$$\text{CH}_2(\text{OCH}_2)_n\text{OH}$$

where n has a value of from about 0 to about 5, and is available under the trade name Nuosept® C from Hüls America. When Nuosept® C is used as the preservative, it is typically present at a level of from about 0.005% to about 0.1%, by weight of the usage composition.

Mixtures of the preferred cyclic organic nitrogen compounds can also be used as the preservative in the present invention.

(4). Low Molecular Weight Aldehydes (a). Formaldehyde

A preferred preservative for use in the present invention is formaldehyde. Formaldehyde is a broad spectrum preservative which is normally available as formalin which is a 37% aqueous solution of formaldehyde. When formaldehyde is used as the preservative in the present invention, typical levels are from about 0.003% to about 0.2%, preferably from about 0.008% to about 0.1% more preferably from about 0.01% to about 0.05%, by weight of the usage composition.

(b) Glutaraldehyde

A preferred preservative for use in the present invention is glutaraldehyde. Glutaraldehyde is a water-soluble, broad spectrum preservative commonly available as a 25% or a 50% solution in water. When glutaraldehyde is used as the preservative in the present invention it is typically present at a level of from about 0.005% to about 0.1%, preferably from about 0.01% to about 0.05%, by weight of the usage composition.

(5). Quaternary Compounds

Preferred preservatives for use in the present invention are cationic and/or quaternary compounds. Such compounds include polyaminopropyl biguanide, also known as polyhexamethylene biguanide having the general formula:

$$\text{HCl.NH}_2\text{—(CH}_2)_3\text{—[—(CH}_2)_3\text{—NH—C(=NH)—NH—C(=NH.HCl)—NH—(CH}_2)_3\text{—]}_x\text{—(CH}_2)_3\text{—NH—C(=NH)—NH.CN}$$

Polyaminopropyl biguanide is a water-soluble, broad spectrum preservative which is available as a 20% aqueous solution available under the trade name Cosmocil CQ® from ICI Americas, Inc., or under the trade name Mikrokill® from Brooks, Inc.

1-(3-Chlorallyl) -3,5,7-triaza-1-azoniaadamantane chloride, available, e.g., under the trade name Dowicil 200 from Dow Chemical, is an effective quaternary ammonium preservative; it is freely soluble in water; however, it has the tendency to discolor (yellow), therefore it is not highly preferred.

Mixtures of the preferred quaternary ammonium compounds can also be used as the preservative in the present invention.

When quaternary ammonium compounds are used as the preservative in the present invention, they are typically present at a level of from about 0.005% to about 0.2%, preferably from about 0.01% to about 0.1%, by weight of the usage composition.

(6). Dehydroacetic Acid

A preferred preservative for use in the present invention is dehydroacetic acid. Dehydroacetic acid is a broad spectrum preservative preferably in the form of a sodium or a potassium salt so that it is water-soluble. This preservative acts more as a biostatic preservative than a biocidal preservative. When dehydroacetic acid is used as the preservative it is typically used at a level of from about 0.005% to about 0.2%, preferably from about 0.008% to about 0.1%, more preferably from about 0.01% to about 0.05%, by weight of the usage composition.

(7). Phenyl and Phenolic Compounds

Some non-limiting examples of phenyl and phenolic compounds suitable for use in the present invention are:

4,4'-diamidino-α,ω-diphenoxypropane diisethionate, commonly known as propamidine isethionate, with water solubility of about 16%; and 4,4'-diamidino-α,ω-diphenoxyhexane diisethionate, commonly known as hexamidine isethionate. Typical effective level of these salts is about 0.0002% to about 0.05% by weight of the usage composition.

Other examples are benzyl alcohol, with a water solubility of about 4%; 2-phenylethanol, with a water solubility of about 2%; and 2-phenoxyethanol, with a water solubility of about 2.67%; typical effective level of these phenyl and phenoxy alcohol is from about 0.1% to about 0.5%, by weight of the usage composition.

(8). Mixtures thereof

The preservatives of the present invention can be used in mixtures in order to control a broad range of microorganisms.

Bacteriostatic effects can sometimes be obtained for aqueous compositions by adjusting the composition pH to an acid pH, e.g., less than about pH 4, preferably less than about pH 3, or a basic pH, e.g., greater than about 10, preferably greater than about 11. Low pH for microbial control is not a preferred approach in the present invention because the low pH can cause chemical degradation of the cyclodextrins. High pH for microbial control is also not preferred because at high pH's, e.g., greater than about 10, preferably greater than about 11, the cyclodextrins can be ionized and their ability to complex with organic materials is reduced. Therefore, aqueous compositions of the present invention should have a pH of from about 3 to about 10, preferably from about 4 to about 8, more preferably from about 4.5 to about 6. The pH is typically adjusted with inorganic molecules to minimize complexation with cyclodextrin.

(9) Mixtures thereof (M) Water Soluble Polymers

Some water-soluble polymers, e.g., water-soluble cationic polymer and water-soluble anionic polymers can be used in the composition of the present invention to provide additional odor control benefits.

a. Cationic polymers, e.g., polyamines

Water-soluble cationic polymers, e.g., those containing amino functionalities, amido functionalities, and mixtures thereof, are useful in the present invention to control certain acid-type odors.

b. Anionic polymers, e.g., polyacrylic acid

Water-soluble anionic polymers, e.g., polyacrylic acids and their water-soluble salts are useful in the present invention to control certain amine-type odors. Preferred polyacrylic acids and their alkali metal salts have an average molecular weight of less than about 20,000, more preferably less than 5,000. Polymers containing sulfonic acid groups, phosphoric acid groups, phosphonic acid groups, and their water-soluble salts, and mixtures thereof, and mixtures with carboxylic acid and carboxylate groups, are also suitable.

Water-soluble polymers containing both cationic and anionic functionalities are also suitable. Examples of these polymers are given in U.S. Pat. No. 4,909,986, issued Mar. 20, 1990 to N. Kobayashi and A. Kawazoe, incorporated herein by reference. Another example of water-soluble polymers containing both cationic and anionic functionalities is a copolymer of dimethyldiallyl ammonium chloride and acrylic acid, commercially available under the trade name Merquat 280® from Calgon.

Preferably, an effective amount of water soluble polymer, especially anionic polymer, e.g. polyacrylic acids or their water soluble salts, at a level of from about 0.001% to about 3%, preferably from about 0.005% to about 2%, more preferably from about 0.01% to about 1% by weight of the composition, for improved odor control benefit.

(N) Carrier

Aqueous solutions that contain up to about 20%, preferably less than about 5% alcohol are preferred for odor control. The use of an aqueous composition improves the speed of formation of the dilute aqueous treatment solution to provide the maximum separation of cyclodextrin molecules on the fabric and thereby maximizes the chance that an odor molecule will interact with a cyclodextrin molecule.

A preferred carrier of the present invention is water. The water which is used can be distilled, deionized, or tap water. Water not only serves as the liquid carrier for the cyclodextrins, but it also facilitates the complexation reaction between the cyclodextrin molecules and any malodorous molecules that are on the fabric when it is treated. It has recently been discovered that water has an unexpected odor controlling effect of its own. It has been discovered that the intensity of the odor generated by some polar, low molecular weight organic amines, acids, and mercaptans is reduced when the odor-contaminated fabrics are treated with an aqueous solution. Not to be bound by theory, it is believed that water solubilizes and depresses the vapor pressure of these polar, low molecular weight organic molecules, thus reducing their odor intensity.

(O) Other Optional Ingredients

The composition of the present invention can optionally contain adjunct odor-controlling materials, enzymes, chelating agents, antistatic agents, insect and moth repelling agents, colorants, especially bluing agents, antioxidants, and mixtures thereof in addition to the cyclodextrin molecules. The total level of optional ingredients is low, preferably less than about 5%, more preferably less than about 3%, and even more preferably less than about 2%, by weight of the usage composition. These optional ingredients exclude the other ingredients specifically mentioned hereinbefore. It is desirable to have more than one odor-controlling material material to enhance the ability to control odors and broaden the range of odor types and molecule sizes which can be controlled. Such materials include, for example, the metallic salts mentioned before, water-soluble cationic and anionic polymers, zeolites, water-soluble bicarbonate salts, and mixtures thereof.

(1). Soluble Carbonate and/or Bicarbonate Salts

Water-soluble alkali metal carbonate and/or bicarbonate salts, such as sodium bicarbonate, potassium bicarbonate, potassium carbonate, cesium carbonate, sodium carbonate, and mixtures thereof can be added to the composition of the present invention in order to help to control certain acid-type odors. Preferred salts are sodium carbonate monohydrate, potassium carbonate, sodium bicarbonate, potassium bicarbonate, and mixtures thereof. When these salts are added to the composition of the present invention, they are typically present at a level of from about 0.1% to about 5%, preferably from about 0.2% to about 3%, more preferably from about 0.3% to about 2%, by weight of the composition. When these salts are added to the composition of the present invention it is preferably that incompatible metal salts not be present in the invention. Preferably, when these salts are used the composition should be essentially free of zinc and other incompatible metal ions, e.g., Ca, Fe, Ba, etc. which form water-insoluble salts.

(2). Enzymes

Enzymes can be used to control certain types of malodor, especially malodor from urine and other types of excretions, including regurgitated materials. Proteases are especially desirable. The activity of commercial enzymes depends very much on the type and purity of the enzyme being considered. Enzymes that are water soluble proteases like pepsin, tripsin, ficin, bromelin, papain, rennin, and mixtures thereof are particularly useful.

Enzymes are normally incorporated at levels sufficient to provide up to about 5 mg by weight, preferably from about 0.001 mg to about 3 mg, more preferably from about 0.002 mg to about 1 mg, of active enzyme per gram of the aqueous compositions. Stated otherwise, the aqueous compositions herein can comprise from about 0.0001% to about 0.5%, preferably from about 0.001% to about 0.3%, more preferably from about 0.005% to about 0.2% by weight of a commercial enzyme preparation. Protease enzymes are usually present in such commercial preparations at levels sufficient to provide from 0.0005 to 0.1 Anson units (AU) of activity per gram of aqueous composition.

Nonlimiting examples of suitable, commercially available, water soluble proteases are pepsin, tripsin, ficin, bromelin, papain, rennin, and mixtures thereof. Papain can be isolated, e.g., from papaya latex, and is available commercially in the purified form of up to, e.g., about 80% protein, or cruder, technical grade of much lower activity. Other suitable examples of proteases are the subtilisins which are obtained from particular strains of *B. subtilis* and *B. licheniforms*. Another suitable protease is obtained from a strain of Bacillus, having maximum activity throughout the pH range of 8–12, developed and sold by Novo Industries A/S under the registered trade name ESPERASE®. The preparation of this enzyme and analogous enzymes is described in British Patent Specification No. 1,243,784 of Novo. Proteolytic enzymes suitable for removing protein-based stains that are commercially available include those sold under the trade names ALCALASE® and SAVINASE® by Novo Industries A/S (Denmark) and MAXATASE® by International Bio-Synthetics, Inc. (The Netherlands). Other proteases include Protease A (see European Patent Application 130,756, published Jan. 9, 1985); Protease B (see European Patent Application Serial No. 87303761.8, filed Apr. 28, 1987, and European Patent Application 130,756, Bott et al, published Jan. 9, 1985); and proteases made by Genencor International, Inc., according to one or more of the following patents: Caldwell et al, U.S. Pat. Nos. 5,185,258, 5,204,015 and 5,244,791.

A wide range of enzyme materials and means for their incorporation into liquid compositions are also disclosed in U.S. Pat. No. 3,553,139, issued Jan. 5, 1971 to McCarty et al. Enzymes are further disclosed in U.S. Pat. No. 4,101,457, Place et al, issued Jul. 18, 1978, and in U.S. Pat. No. 4,507,219, Hughes, issued Mar. 26, 1985. Other enzyme materials useful for liquid formulations, and their incorporation into such formulations, are disclosed in U.S. Pat. No. 4,261,868, Hora et al, issued Apr. 14, 1981. Enzymes can be stabilized by various techniques, e.g., those disclosed and exemplified in U.S. Pat. No. 3,600,319, issued Aug. 17, 1971 to Gedge, et al., European Patent Application Publication No. 0 199 405, Application No. 86200586.5, published Oct. 29, 1986, Venegas, and in U.S. Pat. No. 3,519,570. All of the above patents and applications are incorporated herein, at least in pertinent part.

Enzyme-polyethylene glycol conjugates are also preferred. Such polyethylene glycol (PEG) derivatives of enzymes, wherein the PEG or alkoxy-PEG moieties are coupled to the protein molecule through, e.g., secondary amine linkages. Suitable derivatization decreases immunogenicity, thus minimizes allergic reactions, while still maintains some enzymatic activity. An example of protease-PEG's is PEG-subtilisin Carlsberg from *B. lichen-niformis* coupled to methoxy-PEGs through secondary amine linkage, and is available from Sigma-Aldrich Corp., St Louis, Mo. Rick, Yes, although they are not compatible with surfactants, In an additive, they might work quite well.

(3). Antistatic Agents

The composition of the present invention can optionally contain an effective amount of antistatic agent to provide the treated clothes with in-wear static control. Preferred antistatic agents are those that are water soluble in at least an effective amount, such that the composition remains a clear solution, and are compatible with cyclodextrin. Nonlimiting examples of these antistatic agents are polymeric quaternary ammonium salts, such as polymers conforming to the general formula:

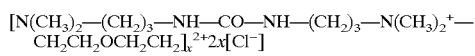

available under the trade name Mirapol A-15® from Rhône-Poulenc, and

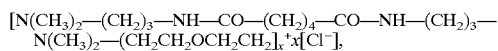

available under the trade name Mirapol AD-1® from Rhône-Poulenc, quaternized polyethyleneimines, vinylpyrrolidone/methacrylam idopropyltrimethylammonium chloride copolymer, available under the trade name Gafquat HS-100® from GAF; triethonium hydrolyzed collagen ethosulfate, available under the trade name Quat-Pro E® from Maybrook; neutralized sulfonated polystyrene, available, e.g., under the trade name Versa TL-130® from Alco Chemical, neutralized sulfonated styrene/maleic anhydride copolymers, available, e.g., under the trade name Versa TL-4® from Alco Chemical; polyethylene glycols; and mixtures thereof.

It is preferred that a no foaming, or low foaming, agent is used, to avoid foam formation during fabric treatment. It is also preferred that polyethoxylated agents such as polyethylene glycol or Variquat 66® are not used when alpha-cyclodextrin is used. The polyethoxylate groups have a strong affinity to, and readily complex with, alpha-cyclodextrin which in turn depletes the uncomplexed cyclodextrin available for odor control.

When an antistatic agent is used it is typically present at a level of from about 0.05% to about 10%, preferably from about 0.1% to about 5%, more preferably from about 0.3% to about 3%, by weight of the usage composition.

(4). Insect and/or Moth Repelling Agent

The composition of the present invention can optionally contain an effective amount of insect and/or moth repelling agents. Typical insect and moth repelling agents are pheromones, such as anti-aggregation pheromones, and other natural and/or synthetic ingredients. Preferred insect and moth repellent agents useful in the composition of the present invention are perfume ingredients, such as citronellol, citronellal, citral, linalool, cedar extract, geranium oil, sandalwood oil, 2-(diethylphenoxy)ethanol, 1-dodecene, etc. Other examples of insect and/or moth repellents useful in the composition of the present invention are disclosed in U.S. Pat. Nos. 4,449,987; 4,693,890; 4,696,676; 4,933,371; 5,030,660; 5,196,200; and in "Semio Activity of Flavor and Fragrance Molecules on Various Insect Species", B. D. Mookherjee et al., published in *Bioactive Volatile Compounds from Plants*, ASC Symposium Series 525, R. Teranishi, R. G. Buttery, and H. Sugisawa, 1993, pp. 35–48, all of said patents and publications being incorporated herein by reference. When an insect and/or moth repellent is used it is typically present at a level of from about 0.005% to about 3%, by weight of the usage composition.

(5). Additional Odor Absorbers

When the clarity of the solution is not needed, other optional odor absorbing materials, e.g., zeolites and/or activated carbon, can also be used.

(a). Zeolites

A preferred class of zeolites is characterized as "intermediate" silicate/aluminate zeolites. The intermediate zeolites are characterized by $SiO_2/AlO_2$ molar ratios of less than about 10. Preferably the molar ratio of $SiO_2/AlO_2$ ranges from about 2 to about 10. The intermediate zeolites have an advantage over the "high" zeolites. The intermediate zeolites have a higher affinity for amine-type odors, they are more weight efficient for odor absorption because they have a larger surface area, and they are more moisture tolerant and retain more of their odor absorbing capacity in water than the high zeolites. A wide variety of intermediate zeolites suitable for use herein are commercially available as Valfor® CP301-68, Valfor® 300-63, Valfor® CP300-35, and Valfor® CP300-56, available from PQ Corporation, and the CBV100® series of zeolites from Conteka.

Zeolite materials marketed under the trade name Abscents® and Smellrite®, available from The Union Carbide Corporation and UOP are also preferred. These materials are typically available as a white powder in the 3–5 micron particle size range. Such materials are preferred over the intermediate zeolites for control of sulfur-containing odors, e.g., thiols, mercaptans.

(b). Activated Carbon

The carbon material suitable for use in the present invention is the material well known in commercial practice as an absorbent for organic molecules and/or for air purification purposes. Often, such carbon material is referred to as "activated" carbon or "activated" charcoal. Such carbon is available from commercial sources under such trade names as; Calgon-Type CPG®; Type PCB®; Type SGL®; Type CAL®; and Type OL®.

(6). Colorant

Colorants and dyes, especially bluing agents, can be optionally added to the odor absorbing compositions for visual appeal and performance impression. When colorants are used, they are used at extremely low levels to avoid fabric staining. Preferred colorants for use in the present compositions are highly water-soluble dyes, e.g., Liquitint® dyes available from Milliken Chemical Co. Non-limiting examples of suitable dyes are, Liquitint Blue HP®, Liquitint Blue 65®, Liquitint Patent Blue®, Liquitint Royal Blue®, Liquitint Experimental Yellow 8949-43®, Liquitint Green HMC®, Liquitint Yellow II®, and mixtures thereof, preferably Liquitint Blue HP®, Liquitint Blue 65®, Liquitint Patent Blue®, Liquitint Royal Blue®, Liquitint Experimental Yellow 8949-43®, and mixtures thereof.

III. Article of Manufacture

The composition of the present invention can also be used in an article of manufacture comprising said composition plus instructions that the composition be used in one, or more steps of a laundry process to remove/eliminate/reduce the effect of malodor on the laundry. When the commercial embodiment of the article of manufacture is used, it is optional, but preferable, to include the preservative, especially when the cyclodextrin is present. Therefore, the most basic article of manufacture comprises uncomplexed cyclodextrin, a carrier, and the package with the instructions. The instructions can comprise instructions to follow any, or all of the methods disclosed hereinbefore and/or to use the composition to provide a given benefit as described hereinbefore.

All percentages, ratios, and parts herein, in the Specification, Examples, and Claims are by weight and are approximations unless otherwise stated.

The following are non-limiting examples of the instant composition. The perfumes in the examples can be any one of the following.

| PERFUME INGREDIENTS | |
|---|---|
| PERFUME | A Wt. % |
| 4-TERTIARY BUTYL CYCLOHEXYL ACETATE | 5.00 |
| BENZOPHENONE | 3.00 |
| BENZYL SALICYLATE | 5.00 |
| CIS-3-HEXENYL SALICYLATE | 1.20 |
| CYMAL | 5.00 |
| DECYL ALDERYDE | 0.10 |
| DIHYDRO MYRCENOL | 2.00 |
| DIMETHYL BENZYL CARBINYL ACETATE | 0.50 |
| FLOR ACETATE | 3.00 |
| FLORHYDRAL | 0.40 |
| GALAXOLIDE 50 DEP | 15.00 |
| HELIONAL | 3.00 |
| HEXYL CINNAMIC ALDEHYDE | 10.00 |
| LINALOOL | 4.80 |
| METHYL DIHYDRO JASMONATE | 15.00 |
| ORANGE TERPENES | 1.20 |
| LYRAL | 25.00 |
| UNDECYLENIC ALDEHYDE | 0.50 |
| VANILLIN | 0.30 |
| TOTAL | 100.00 |

| PERFUME | B Wt. % | C Wt. % |
|---|---|---|
| BETA GAMMA HEXENOL | 0.35 | 0.00 |
| CETALOX | 0.05 | 0.05 |
| CIS-3-HEXENYL SALICYLATE | 2.70 | 1.00 |
| CITRAL | 0.35 | 0.00 |
| CITRONELLAL NITRILE | 2.00 | 2.50 |
| CITRONELLOL | 4.00 | 4.00 |
| COUMARIN | 0.70 | 0.70 |
| DAMASCONE BETA | 0.05 | 0.20 |
| DECYL ALDEHYDE | 0.50 | 0.35 |
| DIHYDRO MYRCENOL | 0.70 | 2.00 |
| FLOR ACETATE | 7.00 | 7.00 |
| FRUTENE | 5.00 | 5.00 |
| GALAXOLIDE 50 IPM | 14.00 | 20.00 |
| HELIONAL | 2.00 | 2.00 |
| HEXYL CINNAMIC ALDEHYDE | 17.00 | 13.00 |
| HEXYL SALICYLATE | 3.00 | 0.00 |
| MENTHOL | 0.05 | 0.00 |
| METHYL ANTHRANILATE | 2.00 | 5.00 |
| METHYL CEDRYLONE | 5.00 | 5.00 |
| METHYL DIHYDRO JASMONATE | 3.50 | 5.00 |
| METHYL DIOXOLAN | 6.00 | 3.00 |
| METHYL ISO BUTENYL TETRAHYDRO PYRAN | 0.20 | 0.10 |
| METHYL PHENYL CARBINYL ACETATE | 0.50 | 0.50 |
| ORANGE TERPENES | 2.50 | 2.50 |
| LYRAL | 10.00 | 10.00 |
| PARA HYDROXY PHENYL BUTANONE | 2.00 | 1.00 |
| PRENYL ACETATE | 1.00 | 1.00 |
| SANDALORE | 0.20 | 1.20 |
| TRIPLAL | 0.20 | 0.50 |
| UNDECALACTONE | 4.00 | 4.00 |
| VERDOX | 3.45 | 3.40 |
| Total | 100.00 | 100.00 |

-continued

PERFUME INGREDIENTS

| PERFUME | D Wt. % |
|---|---|
| ISO-E SUPER | 5.00 |
| AURANTIOL | 1.00 |
| BENZYL SALICYLATE | 14.65 |
| CETALOX | 0.20 |
| CIS 3 HEXENYL ACETATE | 0.50 |
| CITRONELLOL | 2.00 |
| DIPHENYL OXIDE | 0.70 |
| ETHYL VANILLIN | 0.40 |
| EUGENOL | 0.70 |
| EXALTEX | 1.20 |
| FLOR ACETATE | 2.30 |
| GALAXOLIDE 50 DEP | 9.00 |
| GAMMA DECALACTONE | 0.25 |
| GERANIOL | 2.50 |
| GERANYL NITRILE | 0.70 |
| HEXYL CINNAMIC ALDEHYDE | 10.00 |
| INDOL | 0.05 |
| LINALOOL | 5.00 |
| LINALYL ACETATE | 2.80 |
| LRG 201 | 1.25 |
| METHYL BETA-NAPHTHYL KETONE | 1.90 |
| METHYL CEDRYLONE | 14.00 |
| METHYL ISO BUTENYL TETRAHYDRO PYRAN | 0.10 |
| MUSK PLUS | 6.00 |
| ORANGE TERPENES | 0.70 |
| LYRAL | 12.00 |
| PATCHON | 1.80 |
| PHENYL ETHYL PHENYL ACETATE | 1.00 |
| SANDALORE | 2.30 |
| Total | 100.00 |

| PERFUME | E Wt. % |
|---|---|
| HEXYL CINNAMIC ALDEHYDE | 12.65 |
| ANISIC ALDEHYDE | 0.55 |
| BENZALDEHYDE | 0.55 |
| BENZYL SALICYLATE | 10.00 |
| BUTYL CINNAMIC ALDEHYDE | 1.10 |
| CIS 3 HEXENYL ACETATE | 0.75 |
| CIS-3-HEXENYL SALICYLATE | 8.20 |
| COUMARIN | 3.25 |
| DIHYDRO ISO JASMONATE | 8.20 |
| ETHYL-2-METHYL BUTYRATE | 0.55 |
| ETHYLENE BRASSYLATE | 11.00 |
| FRUCTONE | 0.55 |
| GALAXOLIDE 50 DEP | 11.00 |
| GAMMA DECALACTONE | 4.35 |
| HEXYL ACETATE | 1.10 |
| LINALOOL | 10.00 |
| AURANTIOL | 2.15 |
| NONALACTONE | 1.10 |
| TRIPLAL | 0.30 |
| UNDECALACTONE | 11.00 |
| UNDECAVERTOL | 0.55 |
| VANILLIN | 1.10 |
| TOTAL | 100.00 |

| PERFUME | F Wt. % |
|---|---|
| ISO-E SUPER | 7.000 |
| ALPHA DAMASCONE | 0.350 |
| AURANTIOL | 3.200 |
| BETA NAPHTHOL METHYL ETHER | 0.500 |
| CETALOX | 0.250 |
| CIS JASMONE | 0.300 |
| CIS-3-HEXENYL SALICYLATE | 0.500 |
| CITRONELLAL NITRILE | 1.500 |
| CITRONELLOL | 1.600 |
| COUMARIN | 0.400 |
| DIPHENYL OXIDE | 0.150 |

-continued

PERFUME INGREDIENTS

| ETHYL-2-METHYL BUTYRATE | 0.010 |
|---|---|
| EUCALYPTOL | 0.650 |
| EXALTOLIDE | 0.500 |
| FLOR ACETATE | 2.000 |
| FLORALOZONE | 1.500 |
| FLORHYDRAL | 0.400 |
| GALAXOLIDE 50 IPM | 9.350 |
| HEXYL CINNAMIC ALDEHYDE | 7.000 |
| HEXYL SALICYLATE | 5.000 |
| INTRELEVEN ALDEHYDE SP | 0.450 |
| IONONE GAMMA METHYL | 4.150 |
| LIGUSTRAL | 0.600 |
| LINALOOL | 1.400 |
| LINALYL ACETATE | 1.400 |
| LRG 201 | 0.400 |
| LYMOLENE | 1.000 |
| METHYL ANTHRANILATE | 2.250 |
| METHYL BETA-NAPHTHYL KETONE | 0.650 |
| METHYL CEDRYLONE | 5.000 |
| METHYL ISO BUTENYL TETRAHYDRO PRYAN | 0.200 |
| ORANGE TERPENES | 7.200 |
| LYRAL | 12.200 |
| PHENOXANOL | 6.950 |
| PHENYL ETHYL ACETATE | 0.350 |
| SANDALORE | 1.940 |
| TETRA HYDRO LINALOOL | 4.200 |
| TONALID | 7.150 |
| UNDECALACTONE | 0.350 |
| TOTAL | 100.00 |

| PERFUME | G Wt. % |
|---|---|
| MYRCENE | 0.15 |
| ORANGE TERPENES | 1.25 |
| DIHYDRO MYRCENOL | 10.60 |
| CYCLAL C | 0.15 |
| PHENYL ETHYL ALCOHOL | 7.70 |
| BENZYL ACETATE | 0.10 |
| NEROL | 1.65 |
| GERANIOL | 1.75 |
| METHYL ANTHRANILATE | 0.95 |
| VANILLIN | 3.25 |
| LYRAL | 32.00 |
| ISO E SUPER | 12.40 |
| LRG 201 | 6.50 |
| HEXYL CINNAMIC ALDEHYDE | 15.15 |
| ethyl methyl phenyl glycidate | 0.40 |
| DIHYDRO ISO JASMONATE | 5.00 |
| METHYL CEDRYLONE | 1.00 |
| TOTAL | 100.00 |

| PERFUME | H Wt. % |
|---|---|
| BENZYL ACETATE | 3.00 |
| BENZYL SALICYLATE | 20.00 |
| BETA GAMMA HEXENOL | 0.10 |
| CEDRAMBER | 0.75 |
| CETALOX | 0.20 |
| CIS JASMONE | 0.20 |
| CIS-3-HEXENYL SALICYLATE | 1.50 |
| COUMARIN | 1.30 |
| DAMASCENONE | 0.10 |
| DIHYDRO ISO JASMONATE | 5.00 |
| ETHYLENE BRASSYLATE | 5.00 |
| EXALTOLIDE | 3.00 |
| FRUCTONE | 0.35 |
| FRUTENE | 2.00 |
| GAMMA DECALACTONE | 0.30 |
| HEXYL CINNAMIC ALDEHYDE | 12.50 |
| HEXYL SALICYLATE | 10.00 |
| indol | 0.10 |
| ISO E SUPER | 6.80 |
| ISO EUGENOL | 0.30 |

| PERFUME INGREDIENTS | |
|---|---|
| LACTOJASMON | 0.10 |
| LRG 201 | 0.50 |
| METHYL ANTHRANILATE | 1.00 |
| METHYL DIHYDRO JASMONATE | 6.00 |
| ORANGE TERPENES | 1.00 |
| LYRAL | 8.00 |
| PARA CRESYL METHYL ETHER | 0.20 |
| PHENYL ETHYL ALCOHOL | 2.00 |
| SANDALORE | 3.00 |
| TRIMOFIX O | 4.50 |
| UNDECALACTONE | 0.30 |
| UNDECAVERTOL | 0.30 |
| VANILLIN | 0.40 |
| VERDOX | 0.20 |
| TOTAL | 100.00 |

The following are non-limiting examples of the instant composition. The following compositions are prepared by first making a clear premix containing ethanol, diethylene glycol, perfume, and Silwet L-7600 surfactant to insure that all perfume ingredients are pre-dissolved. In examples II, III, and IV, the stability aid, such as hydrophobic/hydrophilic copolymer, or vesicle forming agent, is added during the premix stage. In the main mix tank, hydroxypropyl beta cyclodextrin (HPBCD) and 98% of the water are first mixed with moderate agitation for about 10 minutes. In the case of example I, this is followed by adding polyacrylate acid and Kathon with an additional 10 minutes of mixing. The clear premix is then added to the main mix slowly into the vortex with vigorous agitation for about 30 minutes so that a stable emulsion/dispersion is formed. pH trim with either HCl or NaOH and water hold are added last with final mixing under moderate conditions for about 30 minutes.

| Examples Ingredients | I Wt % | II Wt % | III Wt % | IV Wt % | V Wt % | VI Wt % |
|---|---|---|---|---|---|---|
| Premix | | | | | | |
| Ethanol | | 3.0 | 3.0 | 3.0 | 3.0 | 5.0 |
| Diethylene glycol | | 1.0 | 0.5 | | | |
| Perfume | 0.2 | 0.3 | 0.2 | 0.2 | 0.3 | 0.3 |
| Silwet L-7600 | 1.0 | 1.0 | 1.0 | 1.0 | 1.0 | 1.0 |
| Odor blocker 4-cyclohexyl-4-methyl-2-pentanone | | | | 0.1 | | 0.05 |
| Class I and II Aldehyde, mixture of ethyl-vanillin & Hexyl-cinnamic aldehyde | | | | 0.2 | | 0.1 |
| Main Mix | | | | | | |
| HPBCD$^{(a) \text{ or } (b)}$ | 5.0 | 10.0 | 5.0 | 10.0 | 5.0 | 3.0 |
| Sodium Polyacrylate (2500 M.W.) | 1.0 | | | | | |
| Bardac 2250 (quats) | | | | | 1.0 | |
| Kathon | 3 ppm | 3 ppm | 3 ppm | 3 ppm | 3 ppm | 3 ppm |
| HCl or NaOH | to pH 6 | to pH 7 | to pH 4 | to pH 9 | to pH 4 | to pH 4 |
| Distilled water | Bal. | Bal. | Bal. | Bal. | Bal. | Bal. |
| Total | 100 | 100 | 100 | 100 | 100 | 100 |

| Examples Ingredients | VII Wt % | VIII Wt % | IX Wt % | X Wt % | XI Wt % |
|---|---|---|---|---|---|
| Premix | | | | | |
| Ethanol | 5.0 | 3.0 | 3.0 | | 7.0 |
| Diethylene glycol | 0.5 | | | | 0.2 |
| Perfume | 0.1 | 0.2 | 0.2 | 0.1 | 0.1 |
| Silwet L-7600 | 1.0 | 1.0 | 1.0 | 1.0 | 1.0 |
| Odor blocker 4-cyclohexyl-4-methyl-2-pentanone | | | | | |
| Class I and II Aldehyde | | | | | |
| Hexyl-cinnamic aldehyde | | | | | |
| Flavanoids | | | | | 0.5 |
| Main Mix | | | | | |
| HPBCD$^{(a) \text{ or } (b)}$ | 7.0 | 5.0 | 5.0 | 5.0 | 7.0 |
| Sodium Polyacrylate (2500 M.W.) | | | | | |
| Zinc chloride | | | 1.0 | | |
| Sodium bicarbonate | | | | 2.0 | |
| Bardac 2250 (quats) | 0.5 | | | | |
| Kathon | 3 ppm | 3 ppm | 3 ppm | 3 ppm | 3 ppm |
| HCl or NaOH | to pH 5 | to pH 11 | to pH 4.5 | to pH 5 | to pH 6 |
| Distilled water | Bal. | Bal. | Bal. | Bal. | Bal. |
| Total | 100 | 100 | 100 | 100 | 100 |

| Examples Ingredients | XII Wt % | XIII Wt % | XIV Wt % | XV Wt % | XVI Wt % | XVII Wt % |
|---|---|---|---|---|---|---|
| Premix | | | | | | |
| Ethanol | 3.0 | 3.0 | 3.0 | 3.0 | 5.0 | 5.0 |
| Diethylene glycol | 0.1 | 0.1 | 0.1 | 0.1 | 0.1 | 0.3 |
| Perfume | 0.1 | 0.1 | 0.1 | 0.1 | 0.1 | 0.1 |
| Silwet L-7600 | 0.1 | 0.1 | 0.1 | 0.1 | 0.1 | 0.2 |
| AA/TBA copolymer | | 0.1–0.5 | | | | |
| Dialkyl ether quaternary ammonium surfactant | | | 0.5 | | | |
| Acrylates/acrylamide copolymer | | | | | 0.1–0.5 | |
| Main Mix | | | | | | |
| HPBCD$^{(a) \text{ or } (b)}$ | 1.0 | 1.0 | 1.0 | 1.0 | 1.0 | 3.0 |
| Sodium Polyacrylate (2500 M.W.) | 0.2 | | | | | |
| Bardac 2250 (quats) | | | | | 0.15 | |
| Kathon | 3 ppm | 3 ppm | 3 ppm | 3 ppm | 3 ppm | 3 ppm |
| HCl or NaOH | to pH 4 | to pH 7 | to pH 4 | to pH 9 | to pH 4 | to pH 4 |
| Distilled water | Bal. | Bal. | Bal. | Bal. | Bal. | Bal. |
| Total | 100 | 100 | 100 | 100 | 100 | 100 |

| Examples Ingredients | XVIII Wt % | XIX Wt % | XX Wt % | XXI Wt % | XXII Wt % |
|---|---|---|---|---|---|
| Premix | | | | | |
| Ethanol | 0 to 5 | 0 to 5 | 0 to 5 | 0 to 5 | 0 to 5 |
| Diethylene glycol | | | | | |
| Perfume | 0.2 | 0.1 | 0.2 | 0.2 | 0.2 |
| Silwet L-7600 | 1.0 | | | | |
| Silwet L-77 | | | | | 1.0 |
| POE-60 Hydrogenated Caster Oil | | 1.0 | 2.0 | 1.0 | 1.0 |

-continued

| Main Mix | | | | | |
|---|---|---|---|---|---|
| HPBCD[(a) or (b)] | 10.0 | 10.0 | 5.0 | 7.0 | 5.0 |
| Sodium Polyacrylate (2500 M.W.) | 1.0 | 1.0 | 1.0 | | 0.5 |
| Soil Suspending Agent[(c)] | | | 1.0 | | |
| Bardac 2250 (quats) | | | | 1.0 | |
| Proxel GXL | 0.01 | 0.01 | 0.01 | | |
| HCl or NaOH | to pH 5 | to pH 5 | to pH 5 | to pH 5 | to pH 7 |
| Distilled water | Bal. | Bal. | Bal. | Bal. | Bal. |
| Total | 100 | 100 | 100 | 100 | 100 |

[(a)]Hydroxypropyl beta-cyclodextrin.
[(b)]Randomly methylated beta-cyclodextrin.
[(c)]Polyalkyleneimine soil suspending agent.
The perfume is Perfume A.
Silwet L-7600 is a surfactant supplied by Witco Chemical Co..
Flavanoids are plant extracts.
HPBCD[(a) or (b)] is Hydroxyl propyl beta cyclodextrin
Bardac 2250 is C10 dialkyl dimethyl ammonia chloride quat.
Kathon ™ is a preservative.

Hydroxyethyl alpha-cyclodextrin and hydroxyethyl beta-cyclodextrin are obtained as a mixture from the hydroxyethylation reaction of a mixture of alpha-cyclodextrin and beta-cyclodextrin. They can be substituted for the HP-B-CD.

The compositions of the above Examples are added to a typical laundry load containing fabrics with malodor like mechanics uniforms, butcher's aprons, etc. at levels of at least about 20 ppm, and the result is greatly diminished malodor.

What is claimed is:

1. A method of diminishing the effect of malodor that is present on fabric after a conventional washing process comprising adding to at least one step of said washing process a liquid composition comprising an effective amount of malodor counteractant comprising solubilized, uncompleted cyclodextrin.

2. The method of claim 1 wherein said fabrics have a high level of hydrophobic soil.

3. The method of claim 2 wherein said hydrophobic soil is selected from lubricating hydrocarbons including oil and grease and/or vegetable oil, animal oil, and/or body soil.

4. The method of claim 1 wherein said cyclodextrin is present at a level of from about 0.01% to about 60% by weight of the liquid composition.

5. The method of claim 4 wherein said cyclodextrin is present at a level of from about 0.01% to about 20% by weight of the composition.

6. The method of claim 5 wherein said cyclodextrin is present at a level of from about 0.1% to about 10% by weight of the composition.

7. The method of claim 1 wherein said cyclodextrin is selected either from the group consisting of beta-cyclodextrin, alpha-cyclodextrin, gamma-cyclodextrin, derivatives of said cyclodextrins, and mixtures thereof or from the group consisting of methyl substituted cyclodextrins, ethyl substituted cyclodextrins, hydroxyalkyl substituted cyclodextrins, branched cyclodextrins, cationic cyclodextrins, quaternary ammonium cyclodextrins, anionic cyclodextrins, amphoteric cyclodextrins, cyclodextrins wherein at least one glucopyranose unit has a 3-6-anhydro-cyclomalto structure, and mixtures thereof.

8. The method of claim 7 wherein said cyclodextrin is either methylated beta-cyclodextrin; a mixture of methylated alpha-cyclodextrin and methylated beta-cyclodextrin; hydroxypropyl beta-cyclodextrin; or a mixture of hydroxypropyl alpha-cyclodextrin and hydroxypropyl beta-cyclodextrin.

9. A method of diminishing the effect of malodor that is present on fabric after a conventional washing process, said method comprising the step of adding to at least one step of said washing process an effective amount of a liquid composition comprising: (a) solubilized, uncomplexed cyclodextrin and (b) a cyclodextrin-compatible surfactant selected from the group consisting of castor oil surfactant, sorbitan ester surfactant, polyethoxylated fatty alcohol surfactant, glycerol mono-fatty acid ester surfactant, polyethylene glycol fatty acid ester surfactant, fluorocarbon surfactant, and mixtures thereof.

10. The method of claim 9 wherein said cyclodextrin is present at a level of from about 0.01% to about 60% by weight of the liquid composition.

11. The method of claim 10 wherein said cyclodextrin is present at a level of from about 0.01% to about 20% by weight of the composition.

12. The method of claim 11 wherein said cyclodextrin is present at a level of from about 0.1% to about 10% by weight of the composition.

13. The method of claim 9 wherein said cyclodextrin is selected either from the group consisting of beta-cyclodextrin, alpha-cyclodextrin, gamma-cyclodextrin, derivatives of said cyclodextrins, and mixtures thereof or from the group consisting of methyl substituted cyclodextrins, ethyl substituted cyclodextrins, hydroxyalkyl substituted cyclodextrins, branched cyclodextrins, cationic cyclodextrins, quaternary ammonium cyclodextrins, anionic cyclodextrins, amphoteric cyclodextrins, cyclodextrins wherein at least one glucopyranose unit has a 3-6-anhydro-cyclomalto structure, and mixtures thereof.

14. The method of claim 13 wherein said cyclodextrin is either methylated beta-cyclodextrin; a mixture of methylated alpha-cyclodextrin and methylated beta-cyclodextrin; hydroxypropyl beta-cyclodextrin; or a mixture of hydroxypropyl alpha-cyclodextrin and hydroxypropyl beta-cyclodextrin.

15. The method of claim 9 wherein said cyclodextrin-compatible surfactant is present at a level of from about 0.01% to about 2% by weight of the liquid composition.

16. The method of claim 9 wherein said cyclodextrin-compatible surfactant is present at a level of from about 0.1% to about 8% by weight of the liquid composition.

17. A method of diminishing the effect of malodor that is present on fabric after a conventional washing process, said method comprising the step of adding to at least one step of said washing process an effective amount of a composition comprising: (a) solubilized, uncomplexed cyclodextrin and (b) a castor oil surfactant.

18. The method of claim 17 wherein said cyclodextrin is present at a level of from about 0.01% to about 60% by weight of the liquid composition.

19. The method of claim 18 wherein said cyclodextrin is present at a level of from about 0.01% to about 20% by weight of the composition.

20. The method of claim 19 wherein said cyclodextrin is present at a level of from about 0.1% to about 10% by weight of the composition.

21. The method of claim 17 wherein said cyclodextrin is selected either from the group consisting of beta-cyclodextrin, alpha-cyclodextrin, gamma-cyclodextrin, derivatives of said cyclodextrins, and mixtures thereof or from the group consisting of methyl substituted cyclodextrins, ethyl substituted cyclodextrins, hydroxyalkyl substituted cyclodextrins, branched cyclodextrins, cationic cyclodextrins, quaternary ammonium cyclodextrins, anionic cyclodextrins, amphoteric cyclodextrins, cyclodextrins wherein at least one glucopyranose unit has a 3-6-anhydro-cyclomalto structure, and mixtures thereof.

22. The method of claim 21 wherein said cyclodextrin is either methylated beta-cyclodextrin, a mixture of methylated alpha-cyclodextrin and methylated beta-cyclodextrin; hydroxypropyl beta-cyclodextrin; or a mixture of hydroxypropyl alpha-cyclodextrin and hydroxypropyl beta-cyclodextrin.

23. The method of claim 17 wherein said castor oil surfactant is present at a level of from about 0.01% to about 2% by weight of the liquid composition.

24. The method of claim 17 wherein said castor oil surfactant is present at a level of from about 0.1% to about 8% by weight of the liquid composition.

25. The method of claim 17 wherein said castor oil surfactant is a hydrogenated castor oil surfactant.

* * * * *